United States Patent
Wieslander et al.

(10) Patent No.: US 6,241,943 B1
(45) Date of Patent: Jun. 5, 2001

(54) USE OF A SOLUTION COMPRISING GLUCOSE FOR PERITONEAL DIALYSIS HAVING REDUCED FORMATION OF AGE PRODUCTS

(75) Inventors: Anders Wieslander, Lund; Gunita Forsbäck, Löddeköpinge; Torbjörn Linden, Linderöd, all of (SE); Reinhold Deppisch, Hechingen; Thomas Henle, Freising, both of (DE); Anne Dawnay, London (GB)

(73) Assignee: Gambro AB (SE)

( * ) Notice: Subject to any disclaimer, the term of this patent is extended or adjusted under 35 U.S.C. 154(b) by 0 days.

(21) Appl. No.: 09/125,470
(22) PCT Filed: Feb. 19, 1997
(86) PCT No.: PCT/SE97/00272
 § 371 Date: Dec. 1, 1998
 § 102(e) Date: Dec. 1, 1998
(87) PCT Pub. No.: WO97/30694
 PCT Pub. Date: Aug. 28, 1997

(30) Foreign Application Priority Data

Feb. 20, 1996 (SE) .................................................. 9600631

(51) Int. Cl.$^7$ ........................................................ A61L 2/00
(52) U.S. Cl. .................................. 422/1; 422/25; 422/40; 422/41; 422/256; 604/28; 604/29; 604/408; 604/409; 604/410
(58) Field of Search ..................................... 422/1, 25, 40, 422/41, 256; 604/408–410, 28, 29

(56) References Cited

U.S. PATENT DOCUMENTS

| | | | |
|---|---|---|---|
| 5,312,547 | * | 5/1994 | Kruger et al. ........................ 210/317 |
| 5,536,469 | * | 7/1996 | Jonsson et al. ........................... 422/1 |
| 5,643,201 | * | 7/1997 | Peabody et al. ........................ 604/31 |

* cited by examiner

*Primary Examiner*—Krisanne Thornton
(74) *Attorney, Agent, or Firm*—Lerner, David, Littenberg, Krumholz & Mentlik, LLP

(57) ABSTRACT

Use of a solution comprising glucose for peritoneal dialysis, in which the glucose portion is sterilised separately from the remaining components at a high glucose concentration above about 20% and mixed after sterilisation, substantially according to WO 93/09820. The solution has a reduced formation of advanced glycosylation end products and the use is indicated for diabetic uremic patients.

5 Claims, 1 Drawing Sheet

US 6,241,943 B1

USE OF A SOLUTION COMPRISING GLUCOSE FOR PERITONEAL DIALYSIS HAVING REDUCED FORMATION OF AGE PRODUCTS

AREA OF INVENTION

The present invention relates to the use of a solution comprising glucose and intended for peritoneal dialysis and having reduced formation of AGE products.

PRIOR ART

Peritoneal dialysis is a treatment performed when the renal capacity of a patient's kidney is impaired. A peritoneal dialysis solution is installed in the patients abdominal cavity via a catheter and exchange between the blood and the dialysis solution takes place across the peritoneal membrane, whereupon the dialysis solution is drained. In order to obtain fluid removal, the dialysis solution comprises an osmotic agent, usually glucose.

It is known that mixing glucose with amino-containing compounds results in a series of non-enzymatic reactions called Maillard reactions, resulting in advanced glucosylation end products, AGEs. Reference is made to WO 93/13421 and WO 95/30153. It is believed that advanced glucosylation end products are involved in the ageing process of mammals.

Advanced glycosylation end products, AGEs, are known as one candidate to cause diabetic complications. These products are derived from non-enzymatic glycosylation of long-lived proteins that are further modified by the advanced stage of the Maillard reactions, resulting in the formation of glucose-derived cross-links with a brown or fluorescent property. These products increase the vascular permeability by several mechanisms, such as the disturbed integration of basement membrane components due to the cross-linking of proteins, the endothelial cell reaction to the AGE receptor-mediated cytokine release from macrophage, or the occupancy of endothelial cell AGE receptors.

The rise of AGEs is also associated with a variety of tissue disorders including vascular damage, dyslipidaemia and beta-2-microglobuline amyloidosis. Moreover, it has been suggested that elevated AGE levels may mediate the suppression of certain normal host defence mechanisms, such as inhibition of certain bacteriocidal activites.

Advanced glycation has also been implicated in the pathology of Alzheimer's disease.

It has also been suggested that AGE generation is enhanced by an increased oxidative stress associated with uraemia.

Formation of advanced glycosylation end products, AGEs, in connection with peritoneal dialysis has been suggested in an article "In vitro formation of advanced glycation end products in peritoneal dialysis fluid" by Edmund J. Lamb, William R. Cattell and Anne B. St. H. Dawney, published in Kidney International, Vol. 47 (1995) pages 1768–1774 (the expressions "glycosylated" and "glycated" are used interchangeably for the same property). This article investigates peritoneal dialysis solutions of conventional composition in which all components are heat sterilized together as a single solution. The article suggests that such conventional peritoneal dialysis fluid does not contain inhibitors or promoters of the early Maillard reaction other than glucose. The article states that late Maillard reaction products are formed to a higher extent in conventional peritoneal dialysis solutions compared to paired PBS controls. Moreover, the article concludes that such AGE product formation is greater in either fresh dialysis fluid or in dialysate which had been removed from patients immediately after installation, than in dialysates which had remained for longer periods in the peritoneal cavity. The formation of protein-derived fluorescence has been used as a marker of AGE product formation. The article further concludes that results suggest either that conventional peritoneal dialysis fluid contains a factor (or factors) which promotes AGE product formation, and that its concentration diminishes during dialysis, or that the concentration of an inhibitor of the reaction increases in the dialysate during dialysis. In the article it is mentioned that glycation of peritoneal membrane proteins may be involved in the etiology of ultrafiltration failure in CAPD and should the Maillard reaction prove to be relevant to the etiology of ultrafiltration failure, it may be possible to include inhibitors of the reaction in the dialysis fluid, such as aminoguanidine.

WO 93/09820, included herein in its entirety by reference, discloses a peritoneal dialysis solution containing glucose or glucose-like compounds, such as glucose polymers. The disclosed solution is sterilised before use. During sterilisation, the glucose component is sterilized separately from the remaining components at a high concentration of glucose, over 20%, and at a low pH. After sterilisation and preferably shortly before use, the components are mixed to form the final, ready-made peritoneal solution to be installed into the abdomen of the patient. The final solution has a pH of about 6.2–6.5.

Separate sterilization of the concentrated glucose component as described in WO 93/09820 results in a ready-made peritoneal dialysis solution having less break-down products from glucose as compared to a conventional peritoneal dialysis solution.

DISCLOSURE OF THE INVENTION

It could be expected that all peritoneal dialysis solutions comprising glucose should induce AGE formation.

However, it has unexpectedly been discovered that the peritoneal dialysis solution according to WO 93/09820 does not result in formation of AGE products in the same extent as conventional peritoneal dialysis solution. Consequently, a peritoneal dialysis solution according to WO 93/09820 can advantageously be used in patients where formation of AGE products is of importance, such as diabetic patients. Such use will avoid AGE related complications, such as vascular damage, dyslipidaemia and beta-2-microglobuline amyloidosis. Consequently, such use constitutes the second medical use of said peritoneal dialysis solution.

Further features and advantages of the invention will be described in more details below with reference to the appended drawings.

SHORT DESCRIPTION OF THE DRAWINGS

FIG. 1 is a diagram over incubation of two PD solutions and the resultant glycation.

FIG. 2 is a diagram over incubation of the same two PD solutions as in FIG. 1 and the resultant fluorescence generation.

DETAILED DESCRIPTION OF THE INVENTION

Experiments have shown that a peritoneal dialysis (PD) solution according to WO 93/09820, in the following refered to as the PD-BIO solution, results in less formation of late Maillard products during peritoneal dialysis.

FIG. 1 is a diagram according to which a standard PD solution and a PD-BIO solution according to WO 93/09820 are compared.

The standard PD solutions had the following approximate composition in mmol/l: sodium 135, potassium 2, calcium 1,5, magnesium 0,5 and lactate 35. The final glucose concentration was 1,5%. The standard PD solution was comprised in a two litre bag and was sterilised by autoclaving the entire bag. The pH was about 5,5.

The PD-BIO solution had the same final composition. It was comprised in a two litre bag having two separate compartments, one small, upper compartment enclosing only glucose at a concentration of about 50% and at a pH of about 3,2, and a larger, lower compartment enclosing the remaining components at a pH of about 6,7. The bag was autoclaved in this condition. Shortly before use, a frangible pin was broken whereby communication was established between the two compartments and the content of the upper compartment, glucose, was transported to the lower compartment by gravity, thereby forming the final PD solution having a pH of about 6,3.

The samples were buffered to pH 7,4 by the addition of sodium phosphate buffer to a final concentration of 50 mmol/l and was then spiked with HSA (human serum albumin) to an approximate concentration of 1 g/l.

The diagram in FIG. 1 discloses the glycation of the above-mentioned two solutions having a final glucose concentration of 1,5%. As can be seen from the diagram, there is substantially no difference in the glycation rates between the two solutions.

In FIG. 2, the same PD solutions as in FIG. 1 are shown relative to protein fluorescence generation, reflecting AGE formation according to the method described in the above-mentioned article "In vitro formation of advanced glycation end products in peritoneal dialysis fluid". As can clearly be seen, the standard PD fluid has a markedly higher generation of protein fluorescence, compared to the PD-BIO solution.

It is known that pyrraline is a marker for the presence of AGE products. As shown in table I below, the formation of pyrraline was measured for three different solutions, the PD-BIO solution, a conventional PD solution GAMBROSOL and a sterile filtered solution of the same composition as the GAMBROSOL solution, all having a glucose concentration of 4% and the same electrolyte composition as give above.

The samples were incubated for 16 hours or 7 days, at 37° C. under sterile conditions with human serum albumin (A) at a concentration of 40 g/l and without or with addition of 400 mmol/l glucose (G).

TABLE I

| | | pyrralline | |
|---|---|---|---|
| sample | incubation time | µg/g protein | pmol/mg protein |
| PD-BIO | | | |
| 16-A | 16 h | 17 | 67 |
| 7-A | 7 days | 22 | 88 |
| 16-GA | 16 h | 19 | 74 |
| 7-GA | 7 days | 23 | 89 |
| GAMBROSOL | | | |
| 16-A | 16 h | 25 | 97 |
| 7-A | 7 days | 75 | 294 |
| 16-GA | 16 h | 24 | 94 |
| 7-GA | 7 days | 65 | 257 |

TABLE I-continued

| | | pyrralline | |
|---|---|---|---|
| sample | incubation time | µg/g protein | pmol/mg protein |
| Sterile filtered | | | |
| 16-A | 16 h | 17 | 66 |
| 7-A | 7 days | 16 | 65 |
| 16-GA | 16 h | 16 | 63 |
| 7-GA | 7 days | 22 | 86 |

As can be seen from table I, the formation of pyrraline increased by a factor 3 between the 16 hour, incubation and the 7 day inhibation for the GAMBROSOL solution, but was substantially unchanged for the PD-BIO solution and the filtered GAMBROSOL solution.

Although not intended to be limited by any particular theory or hypothesis, it is believed that the above-mentioned data is indicative of the fact that conventional PD solutions sterilised in autoclaves in the final mixed composition, form degradation products of glucose acting as promoters for AGE formation. By the sterilisation method used in the PD-BIO solution, the concentration of such promoters is substantially reduced. This theory seems to be confirmed by the fact that sterile filtered PD solutions of the same composition as the GAMBROSOL solution and the PD-BIO solution do not substantially form pyrraline, as shown in table I.

In table II there is also shown the formation of fructose lysine and pentosidine after 7 days incubation. There seems to be no difference between the three solutions in this regard. Fructose lysine and pentosidine are also markers for AGE products. The conditions were the same as for table I.

TABLE II

| | fructose lysine | | pentosidine | |
|---|---|---|---|---|
| sample | nmol/mg HSA | mmol/mol HSA | pmol/mg HSA | mmol/mol HSA |
| PD-BIO | | | | |
| 7-GA | 79.0 | 5270 | 9.2 | 0.61 |
| 7-A | 35.9 | 2390 | 9.5 | 0.63 |
| GAMBROSOL | | | | |
| 7-GA | 77.6 | 5170 | 10.5 | 0.70 |
| 7-A | 31.2 | 2080 | 9.6 | 0.64 |
| sterile filtered | | | | |
| 7-GA | 73.6 | 4910 | 9.4 | 0.63 |
| 7-A | 36.5 | 2430 | 9.1 | 0.61 |

In order to find out which components in the peritoneal dialysis solution that are responsible for the AGE formation, a series of experiments were carried out, where a sterile filtered PD solution according to the above specifications were used. To the samples of the solution were added human serum albumin at 40 mg/ml as the target protein for AGE formation. In the different samples were added glucose degradation products in different amounts typically found in heat sterilised conventional peritoneal dialysis fluids. The samples were incubated over 0, 1, 10 or 30 days and the AGE formation was measured by fluorescence measurements as in FIG. 2. The results appear from table III below.

TABLE III

|  | t0 | t1 | t10 | t30 |
|---|---|---|---|---|
| Sterile filtered fluid addition of acetaldehyde | 150 | 154 | 169 | 196 |
| 420 µmol | 160 | 169 | 177 | 198 |
| 1573 µmol addition of formaldehyde | 166 | 173 | 188 | 218 |
| 15 µmol | 164 | 171 | 179 | 197 |
| 44 µmol addition of methylglyoxal | 165 | 171 | 181 | 201 |
| 23 µmol | 162 | 165 | 162 | 194 |
| 164 µmol addition of 5-HMF | 154 | 177 | 262 | 295 |
| 30 µmol | 157 | 156 | 164 | 193 |
| 1355 µmol | 157 | 156 | 176 | 219 |
| Autoclaved PD fluid | 160 | 217 | 318 | 371 |

As appears from table III, there seems to be a clear correlation between autoclaved PD fluids (GAMBROSOL) and AGE product formation as indicated by fluorescence. It seems that methylglyoxal also mediates AGE product formation, while the other substances do not seem to have much influence on such production in the used concentrations.

It is known that dicarbonyl compounds and specifically 3-deoxyglycosone, 3-DG, are formed during heat sterilisation of peritoneal dialysis solutions as a glucose degradation product. 3-DG is known to be a potent cross-linker. 3-DG is a highly reactive dicarbonyl intermediate, of the Maillard reactions and a precursor of the advanced glycosylation end products, AGEs, such as pyrraline. The production of 3-DG normally starts from glucose which forms a Schiffs base after reaction with the amino group of a protein. The next step in the Maillard reactions is rearrangement to Amadori products which than in the late Maillard reactions split to form 3-DG. However, 3-DG has also been suggested as a possible intermediate in the degradation of carbohydrates by acids to 2-furaldehyde. If this is possible, 3-DG could appear in fresh fluid for peritoneal dialysis as a glucose degradation product. We have found that dicarbonyl compounds are suppressed at least tenfold in the PD-BIO solution compared to the GAMBROSOL solution.

The above-mentioned data is given for solutions intended to be used for peritoneal dialysis. When such solutions are installed into a patient undergoing peritoneal dialysis treatment, the solution comes into contact with a great number of different proteins prevailing in the peritoneal cavity. Moreover, the solution is diluted with solution already present in the abdominal cavity. Finally, an exchange of electrolytes and molecules take place inside the cavity and notably with the blood through the peritoneal membrane.

During the exposure of the peritoneal cavity to PD solutions having an unphysiologically high concentration of glucose, it is likely that proteins present in the cavity undergo similar reactions as seen in the above examples. Such altered proteins are transported from the abdominal cavity via the peritoneal membrane to the blood and to the rest of the body. Moreover, any precursors or promoters of AGE products can be transported through the periotoneal membrane into the blood.

By using a PD solution having a low concentration of promoters of late stage advanced glycosylation end products, it is likely that adverse effects on the peritoneal membrane can be avoided as well as other complications associated with the generation of AGE products.

What is claimed is:

1. A method for the peritoneal dialysis of a patient susceptible to complications from advanced glycosylation end products comprising preparing a peritoneal dialysis solution by sterilizing a substantially pure glucose solution having a concentration of greater than about 20%, separately preparing a substantially glucose-free composition, and mixing said substantially pure sterilized glucose solution in said substantially glucose-free composition, to produce a solution having a reduced formation of said advanced glycosylation end products.

2. The method of claim 1, wherein said patient comprises a diabetic patient.

3. The method of claim 2, wherein said substantially pure sterilized glucose polymer solution has a concentration of greater than about 40%.

4. A method for the peritoneal dialysis of a patient susceptible to complications from advanced glycosylation end products comprising preparing a peritoneal dialysis solution by filter sterilizing a substantially pure glucose solution, separately preparing a substantially glucose-free composition, and mixing said substantially pure filter sterilized glucose solution in said substantially glucose-free composition to produce a solution having a reduced formation of said advanced glycosylation end products.

5. The method of claim 4, wherein said patient comprises a diabetic patient.

\* \* \* \* \*

UNITED STATES PATENT AND TRADEMARK OFFICE
CERTIFICATE OF CORRECTION

PATENT NO. : 6,241,943 B1
DATED : June 5, 2001
INVENTOR(S) : Wiselander et al.

It is certified that error appears in the above-identified patent and that said Letters Patent is hereby corrected as shown below:

Delete title page and substitute therefore the attached title page.

Delete drawing and substitute therefor the attached drawing sheet.

Delete column 1-6 of the specification and substitute therefor columns 1-6 as per the attached new specification.

Signed and Sealed this

Thirteenth Day of July, 2004

JON W. DUDAS
*Acting Director of the United States Patent and Trademark Office*

(12) United States Patent
Wieslander et al.

(10) Patent No.: US 6,241,943 B1
(45) Date of Patent: Jun. 5, 2001

(54) USE OF A SOLUTION COMPRISING GLUCOSE FOR PERITONEAL DIALYSIS HAVING REDUCED FORMATION OF AGE PRODUCTS

(75) Inventors: Anders Wieslander, Lund; Gunita Forsbäck, Löddeköpinge; Torbjörn Linden, Linderöd, all of (SE); Reinhold Deppisch, Hechingen; Thomas Henle, Freising, both of (DE); Anne Dawnay, London (GB)

(73) Assignee: Gambro AB (SE)

( * ) Notice: Subject to any disclaimer, the term of this patent is extended or adjusted under 35 U.S.C. 154(b) by 0 days.

(21) Appl. No.: 09/125,470

(22) PCT Filed: Feb. 19, 1997

(86) PCT No.: PCT/SE97/00272

§ 371 Date: Dec. 1, 1998

§ 102(e) Date: Dec. 1, 1998

(87) PCT Pub. No.: WO97/30694

PCT Pub. Date: Aug. 28, 1997

(30) Foreign Application Priority Data

Feb. 20, 1996 (SE) .................................................. 9600631

(51) Int. Cl.[7] ........................................................ A61L 2/00
(52) U.S. Cl. ................................ 422/1; 422/25; 422/40; 422/41; 422/256; 604/28; 604/29; 604/408; 604/409; 604/410
(58) Field of Search .................................. 422/1, 25, 40, 422/41, 256; 604/408–410, 28, 29

(56) References Cited

U.S. PATENT DOCUMENTS

| 5,312,547 | * | 5/1994 | Kruger et al. | 210/317 |
| 5,536,469 | * | 7/1996 | Jonsson et al. | 422/1 |
| 5,643,201 | * | 7/1997 | Peabody et al. | 604/31 |

* cited by examiner

Primary Examiner—Krisanne Thornton
(74) Attorney, Agent, or Firm—Lerner, David, Littenberg, Krumholz & Mentlik, LLP

(57) ABSTRACT

Use of a solution comprising glucose for peritoneal dialysis, in which the glucose portion is sterilised separately from the remaining components at a high glucose concentration above about 20% and mixed after sterilisation, substantially according to WO 93/09820. The solution has a reduced formation of advanced glycosylation end products and the use is indicated for diabetic uremic patients.

5 Claims, 1 Drawing Sheet

USE OF A SOLUTION COMPRISING GLUCOSE FOR PERITONEAL DIALYSIS HAVING REDUCED FORMATION OF AGE PRODUCTS

AREA OF INVENTION

The present invention relates to the use of a solution comprising glucose and intended for peritoneal dialysis and having reduced formation of AGE products.

PRIOR ART

Peritoneal dialysis is a treatment performed when the renal capacity of a patient's kidney is impaired. A peritoneal dialysis solution is installed in the patients abdominal cavity via a catheter and exchange between the blood and the dialysis solution takes place across the peritoneal membrane, whereupon the dialysis solution is drained. In order to obtain fluid removal, the dialysis solution comprises an osmotic agent, usually glucose.

It is known that mixing glucose with amino-containing compounds results in a series of non-enzymatic reactions called Maillard reactions, resulting in advanced glucosylation end products, AGEs. Reference is made to WO 93/13421 and WO 95/30153. It is believed that advanced glucosylation end products are involved in the ageing process of mammals.

Advanced glycosylation end products, AGEs, are known as one candidate to cause diabetic complications. These products are derived from non-enzymatic glycosylation of long-lived proteins that are further modified by the advanced stage of the Maillard reactions, resulting in the formation of glucose-derived cross-links with a brown or fluorescent property. These products increase the vascular permeability by several mechanisms, such as the disturbed integration of basement membrane components due to the cross-linking of proteins, the endothelial cell reaction to the AGE receptor-mediated cytokine release from macrophage, or the occupancy of endothelial cell AGE receptors.

The rise of AGEs is also associated with a variety of tissue disorders including vascular damage, dyslipidaemia and beta-2-microglobuline amyloidosis. Moreover, it has been suggested that elevated AGE levels may mediate the suppression of certain normal host defence mechanisms, such as inhibition of certain bacteriocidal activites.

Advanced glycation has also been implicated in the pathology of Alzheimer's disease.

It has also been suggested that AGE generation is enhanced by an increased oxidative stress associated with uraemia.

Formation of advanced glycosylation end products, AGEs, in connection with peritoneal dialysis has been suggested in an article "In vitro formation of advanced glycation end products in peritoneal dialysis fluid" by Edmund J. Lamb, William R. Cattell and Anne B. St. H. Dawney, published in Kidney International, Vol. 47 (1995) pages 1768–1774 (the expressions "glycosylated" and "glycated" are used interchangeably for the same property). This article investigates peritoneal dialysis solutions of conventional composition in which all components are heat sterilized together as a single solution. The article suggests that such conventional peritoneal dialysis fluid does not contain inhibitors or promoters of the early Maillard reaction other than glucose. The article states that late Maillard reaction products are formed to a higher extent in conventional peritoneal dialysis solutions compared to paired PBS controls. Moreover, the article concludes that such AGE product formation is greater in either fresh dialysis fluid or in dialysate which had been removed from patients immediately after installation, than in dialysates which had remained for longer periods in the peritoneal cavity. The formation of protein-derived fluorescence has been used as a marker of AGE product formation. The article further concludes that results suggest either that conventional peritoneal dialysis fluid contains a factor (or factors) which promotes AGE product formation, and that its concentration diminishes during dialysis, or that the concentration of an inhibitor of the reaction increases in the dialysate during dialysis. In the article it is mentioned that glycation of peritoneal membrane proteins may be involved in the etiology of ultrafiltration failure in CAPD and should the Maillard reaction prove to be relevant to the etiology of ultrafiltration failure, it may be possible to include inhibitors of the reaction in the dialysis fluid, such as aminoguanidine.

WO 93/09820, included herein in its entirety by reference, discloses a peritoneal dialysis solution containing glucose or glucose-like compounds, such as glucose polymers. The disclosed solution is sterilised before use. During sterilisation, the glucose component is sterilized separately from the remaining components at a high concentration of glucose, over 20%, and at a low pH. After sterilisation and preferably shortly before use, the components are mixed to form the final, ready-made peritoneal solution to be installed into the abdomen of the patient. The final solution has a pH of about 6.2–6.5.

Separate sterilization of the concentrated glucose component as described in WO 93/09820 results in a ready-made peritoneal dialysis solution having less break-down products from glucose as compared to a conventional peritoneal dialysis solution.

DISCLOSURE OF THE INVENTION

It could be expected that all peritoneal dialysis solutions comprising glucose should induce AGE formation.

However, it has unexpectedly been discovered that the peritoneal dialysis solution according to WO 93/09820 does not result in formation of AGE products in the same extent as conventional peritoneal dialysis solution. Consequently, a peritoneal dialysis solution according to WO 93/09820 can advantageously be used in patients where formation of AGE products is of importance, such as diabetic patients. Such use will avoid AGE related complications, such as vascular damage, dyslipidaemia and beta-2-microglobuline amyloidosis. Consequently, such use constitutes the second medical use of said peritoneal dialysis solution.

Further features and advantages of the invention will be described in more details below with reference to the appended drawings.

SHORT DESCRIPTION OF THE DRAWINGS

FIG. 1 is a diagram over incubation of two PD solutions and the resultant glycation.

FIG. 2 is a diagram over incubation of the same two PD solutions as in FIG. 1 and the resultant fluorescence generation.

DETAILED DESCRIPTION OF THE INVENTION

Experiments have shown that a peritoneal dialysis (PD) solution according to WO 93/09820, in the following refered to as the PD-BIO solution, results in less formation of late Maillard products during peritoneal dialysis.

FIG. 1 is a diagram according to which a standard PD solution and a PD-BIO solution according to WO 93/09820 are compared.

The standard PD solutions had the following approximate composition in mmol/l: sodium 135, potassium 2, calcium 1,5, magnesium 0,5 and lactate 35. The final glucose concentration was 1,5%. The standard PD solution was comprised in a two litre bag and was sterilised by autoclaving the entire bag. The pH was about 5,5.

The PD-BIO solution had the same final composition. It was comprised in a two litre bag having two separate compartments, one small, upper compartment enclosing only glucose at a concentration of about 50% and at a pH of about 3,2, and a larger, lower compartment enclosing the remaining components at a pH of about 6,7. The bag was autoclaved in this condition. Shortly before use, a frangible pin was broken whereby communication was established between the two compartments and the content of the upper compartment, glucose, was transported to the lower compartment by gravity, thereby forming the final PD solution having a pH of about 6,3.

The samples were buffered to pH 7,4 by the addition of sodium phosphate buffer to a final concentration of 50 mmol/l and was then spiked with HSA (human serum albumin) to an approximate concentration of 1 g/l.

The diagram in FIG. 1 discloses the glycation of the above-mentioned two solutions having a final glucose concentration of 1,5%. As can be seen from the diagram, there is substantially no difference in the glycation rates between the two solutions.

In FIG. 2, the same PD solutions as in FIG. 1 are shown relative to protein fluorescence generation, reflecting AGE formation according to the method described in the above-mentioned article "In vitro formation of advanced glycation end products in peritoneal dialysis fluid". As can clearly be seen, the standard PD fluid has a markedly higher generation of protein fluorescence, compared to the PD-BIO solution.

It is known that pyrraline is a marker for the presence of AGE products. As shown in table I below, the formation of pyrraline was measured for three different solutions, the PD-BIO solution, a conventional PD solution GAMBROSOL and a sterile filtered solution of the same composition as the GAMBROSOL solution, all having a glucose concentration of 4% and the same electrolyte composition as give above.

The samples were incubated for 16 hours or 7 days, at 37° C. under sterile conditions with human serum albumin (A) at a concentration of 40 g/l and without or with addition of 400 mmol/l glucose (G).

TABLE I

| | | pyrralline | |
|---|---|---|---|
| sample | incubation time | µg/g protein | pmol/mg protein |
| PD-BIO | | | |
| 16-A | 16 h | 17 | 67 |
| 7-A | 7 days | 22 | 88 |
| 16-GA | 16 h | 19 | 74 |
| 7-GA | 7 days | 23 | 89 |
| GAMBROSOL | | | |
| 16-A | 16 h | 25 | 97 |
| 7-A | 7 days | 75 | 294 |
| 16-GA | 16 h | 24 | 94 |
| 7-GA | 7 days | 65 | 257 |

TABLE I-continued

| | | pyrralline | |
|---|---|---|---|
| sample | incubation time | µg/g protein | pmol/mg protein |
| Sterile filtered | | | |
| 16-A | 16 h | 17 | 66 |
| 7-A | 7 days | 16 | 65 |
| 16-GA | 16 h | 16 | 63 |
| 7-GA | 7 days | 22 | 86 |

As can be seen from table I, the formation of pyrraline increased by a factor 3 between the 16 hour, incubation and the 7 day inhibation for the GAMBROSOL solution, but was substantially unchanged for the PD-BIO solution and the filtered GAMBROSOL solution.

Although not intended to be limited by any particular theory or hypothesis, it is believed that the above-mentioned data is indicative of the fact that conventional PD solutions sterilised in autoclaves in the final mixed composition, form degradation products of glucose acting as promoters for AGE formation. By the sterilisation method used in the PD-BIO solution, the concentration of such promoters is substantially reduced. This theory seems to be confirmed by the fact that sterile filtered PD solutions of the same composition as the GAMBROSOL solution and the PD-BIO solution do not substantially form pyrraline, as shown in table I.

In table II there is also shown the formation of fructose lysine and pentosidine after 7 days incubation. There seems to be no difference between the three solutions in this regard. Fructose lysine and pentosidine are also markers for AGE products. The conditions were the same as for table I.

TABLE II

| | fructose lysine | | pentosidine | |
|---|---|---|---|---|
| sample | mmol/mg HSA | mmol/mol HSA | pmol/mg HSA | mmol/mol HSA |
| PD-BIO | | | | |
| 7-GA | 79.0 | 5270 | 9.2 | 0.61 |
| 7-A | 35.9 | 2390 | 9.5 | 0.63 |
| GAMBROSOL | | | | |
| 7-GA | 77.6 | 5170 | 10.5 | 0.70 |
| 7-A | 31.2 | 2080 | 9.6 | 0.64 |
| sterile filtered | | | | |
| 7-GA | 73.6 | 4910 | 9.4 | 0.63 |
| 7-A | 36.5 | 2430 | 9.1 | 0.61 |

In order to find out which components in the peritoneal dialysis solution that are responsible for the AGE formation, a series of experiments were carried out, where a sterile filtered PD solution according to the above specifications were used. To the samples of the solution were added human serum albumin at 40 mg/ml as the target protein for AGE formation. In the different samples were added glucose degradation products in different amounts typically found in heat sterilised conventional peritoneal dialysis fluids. The samples were incubated over 0, 1, 10 or 30 days and the AGE formation was measured by fluorescence measurements as in FIG. 2. The results appear from table III below.

TABLE III

| | t0 | t1 | t10 | t30 |
|---|---|---|---|---|
| Sterile filtered fluid | 150 | 154 | 169 | 196 |
| addition of acetaldehyde | | | | |
| 420 μmol | 160 | 169 | 177 | 198 |
| 1573 μmol | 166 | 173 | 188 | 218 |
| addition of formaldehyde | | | | |
| 15 μmol | 164 | 171 | 179 | 197 |
| 44 μmol | 165 | 171 | 181 | 201 |
| addition of methylglyoxal | | | | |
| 23 μmol | 162 | 165 | 162 | 194 |
| 164 μmol | 154 | 177 | 262 | 295 |
| addition of 5-HMF | | | | |
| 30 μmol | 157 | 156 | 164 | 193 |
| 1355 μmol | 157 | 156 | 176 | 219 |
| Autoclaved PD fluid | 160 | 217 | 318 | 371 |

As appears from table III, there seems to be a clear correlation between autoclaved PD fluids (GAMBROSOL) and AGE product formation as indicated by fluorescence. It seems that methylglyoxal also mediates AGE product formation, while the other substances do not seem to have much influence on such production in the used concentrations.

It is known that dicarbonyl compounds and specifically 3-deoxyglycosone, 3-DG, are formed during heat sterilisation of peritoneal dialysis solutions as a glucose degradation product. 3-DG is known to be a potent cross-linker. 3-DG is a highly reactive dicarbonyl intermediate, of the Maillard reactions and a precursor of the advanced glycosylation end products, AGEs, such as pyrraline. The production of 3-DG normally starts from glucose which forms a Schiffs base after reaction with the amino group of a protein. The next step in the Maillard reactions is rearrangement to Amadori products which than in the late Maillard reactions split to form 3-DG. However, 3-DG has also been suggested as a possible intermediate in the degradation of carbohydrates by acids to 2-furaldehyde. If this is possible, 3-DG could appear in fresh fluid for peritoneal dialysis as a glucose degradation product. We have found that dicarbonyl compounds are suppressed at least tenfold in the PD-BIO solution compared to the GAMBROSOL solution.

The above-mentioned data is given for solutions intended to be used for peritoneal dialysis. When such solutions are installed into a patient undergoing peritoneal dialysis treatment, the solution comes into contact with a great number of different proteins prevailing in the peritoneal cavity. Moreover, the solution is diluted with solution already present in the abdominal cavity. Finally, an exchange of electrolytes and molecules take place inside the cavity and notably with the blood through the peritoneal membrane.

During the exposure of the peritoneal cavity to PD solutions having an unphysiologically high concentration of glucose, it is likely that proteins present in the cavity undergo similar reactions as seen in the above examples. Such altered proteins are transported from the abdominal cavity via the peritoneal membrane to the blood and to the rest of the body. Moreover, any precursors or promoters of AGE products can be transported through the periotoneal membrane into the blood.

By using a PD solution having a low concentration of promoters of late stage advanced glycosylation end products, it is likely that adverse effects on the peritoneal membrane can be avoided as well as other complications associated with the generation of AGE products.

What is claimed is:

1. A method for the peritoneal dialysis of a patient susceptible to complications from advanced glycosylation end products comprising preparing a peritoneal dialysis solution by sterilizing a substantially pure glucose solution having a concentration of greater than about 20%, separately preparing a substantially glucose-free composition, and mixing said substantially pure sterilized glucose solution in said substantially glucose-free composition, to produce a solution having a reduced formation of said advanced glycosylation end products.

2. The method of claim 1, wherein said patient comprises a diabetic patient.

3. The method of claim 2, wherein said substantially pure sterilized glucose polymer solution has a concentration of greater than about 40%.

4. A method for the peritoneal dialysis of a patient susceptible to complications from advanced glycosylation end products comprising preparing a peritoneal dialysis solution by filter sterilizing a substantially pure glucose solution, separately preparing a substantially glucose-free composition, and mixing said substantially pure filter sterilized glucose solution in said substantially glucose-free composition to produce a solution having a reduced formation of said advanced glycosylation end products.

5. The method of claim 4, wherein said patient comprises a diabetic patient.

* * * * *

UNITED STATES PATENT AND TRADEMARK OFFICE
CERTIFICATE OF CORRECTION

PATENT NO.    : 6,241,943 B1
DATED         : June 5, 2001
INVENTOR(S)   : Wiselander et al.

It is certified that error appears in the above-identified patent and that said Letters Patent is hereby corrected as shown below:

Delete title page and substitute therefore the attached title page.

Delete drawing and substitute therefor the attached drawing sheet.

Delete column 1-6 of the specification and substitute therefor columns 1-8 as per the attached new specification.

This certificate supersedes Certificate of Correction issued July 13, 2004.

Signed and Sealed this

Twenty-first Day of September, 2004

JON W. DUDAS
*Director of the United States Patent and Trademark Office*

(12) United States Patent
Wieslander et al.

(10) Patent No.: US 6,241,943 B1
(45) Date of Patent: Jun. 5, 2001

(54) USE OF A SOLUTION COMPRISING GLUCOSE FOR PERITONEAL DIALYSIS HAVING REDUCED FORMATION OF AGE PRODUCTS

(75) Inventors: Anders Wieslander, Lund; Gunita Forsbäck, Löddeköpinge; Torbjörn Linden, Lineröd, all of (SE); Reinhold Deppisch, Hechingen; Thomas Henle, Freising, both of (DE); Anne Dawnay, London (GB)

(73) Assignee: Gambro AB (SE)

( * ) Notice: Subject to any disclaimer, the term of this patent is extended or adjusted under 35 U.S.C. 154(b) by 0 days.

(21) Appl. No.: 09/125,470

(22) PCT Filed: Feb. 19, 1997

(86) PCT No.: PCT/SE97/00272

§ 371 Date: Dec. 1, 1998

§ 102(e) Date: Dec. 1, 1998

(87) PCT Pub. No.: WO97/30694

PCT Pub. Date: Aug. 28, 1997

(30) Foreign Application Priority Data

Feb. 20, 1996 (SE) .................................................. 9600631

(51) Int. Cl.[7] .................................................. A61L 2/00
(52) U.S. Cl. .................................. 422/1; 422/25; 422/40; 422/41; 422/256; 604/28; 604/29; 604/408; 604/409; 604/410
(58) Field of Search ................................. 422/1, 25, 40, 422/41, 256; 604/408–410, 28, 29

(56) References Cited

U.S. PATENT DOCUMENTS

| | | | |
|---|---|---|---|
| 5,312,547 | * | 5/1994 | Kruger et al. .................. 210/317 |
| 5,536,469 | * | 7/1996 | Jonsson et al. ................. 422/1 |
| 5,643,201 | * | 7/1997 | Peabody et al. ................ 604/31 |

* cited by examiner

*Primary Examiner*—Krisanne Thornton
(74) *Attorney, Agent, or Firm*—Lerner, David, Littenberg, Krumholz & Mentlik, LLP

(57) ABSTRACT

Use of a solution comprising glucose for peritoneal dialysis, in which the glucose portion is sterilised separately from the remaining components at a high glucose concentration above about 20% and mixed after sterilisation, substantially according to WO 93/09820. The solution has a reduced formation of advanced glycosylation end products and the use is indicated for diabetic uremic patients.

5 Claims, 1 Drawing Sheet

USE OF A SOLUTION COMPRISING GLUCOSE FOR PERITONEAL DIALYSIS HAVING REDUCED FORMATION OF AGE PRODUCTS

AREA OF INVENTION

The present invention relates to the use of a solution comprising glucose and intended for peritoneal dialysis and having reduced formation of AGE products.

PRIOR ART

Peritoneal dialysis is a treatment performed when the renal capacity of a patient's kidney is impaired. A peritoneal dialysis solution is installed in the patients abdominal cavity via a catheter and exchange between the blood and the dialysis solution takes place across the peritoneal membrane, whereupon the dialysis solution is drained. In order to obtain fluid removal, the dialysis solution comprises an osmotic agent, usually glucose.

It is known that mixing glucose with amino-containing compounds results in a series of non-enzymatic reactions called Maillard reactions, resulting in advanced glucosylation end products, AGEs. Reference is made to WO 93/13421 and WO 95/30153. It is believed that advanced glucosylation end products are involved in the ageing process of mammals.

Advanced glycosylation end products, AGEs, are known as one candidate to cause diabetic complications. These products are derived from non-enzymatic glycosylation of long-lived proteins that are further modified by the advanced stage of the Maillard reactions, resulting in the formation of glucose-derived cross-links with a brown or fluorescent property. These products increase the vascular permeability by several mechanisms, such as the disturbed integration of basement membrane components due to the cross-linking of proteins, the endothelial cell reaction to the AGE receptor-mediated cytokine release from macrophage, or the occupancy of endothelial cell AGE receptors.

The rise of AGEs is also associated with a variety of tissue disorders including vascular damage, dyslipidaemia and beta-2-microglobuline amyloidosis. Moreover, it has been suggested that elevated AGE levels may mediate the suppression of certain normal host defence mechanisms, such as inhibition of certain bacteriocidal activites.

Advanced glycation has also been implicated in the pathology of Alzheimer's disease.

It has also been suggested that AGE generation is enhanced by an increased oxidative stress associated with uraemia.

Formation of advanced glycosylation end products, AGEs, in connection with peritoneal dialysis has been suggested in an article "In vitro formation of advanced glycation end products in peritoneal dialysis fluid" by Edmund J. Lamb, William R. Cattell and Anne B. St. H. Dawney, published in Kidney International, Vol. 47 (1995) pages 1768–1774 (the expressions "glycosylated" and "glycated" are used interchangeably for the same property). This article investigates peritoneal dialysis solutions of conventional composition in which all components are heat sterilized together as a single solution. The article suggests that such conventional peritoneal dialysis fluid does not contain inhibitors or promoters of the early Maillard reaction other than glucose. The article states that late Maillard reaction products are formed to a higher extent in conventional peritoneal dialysis solutions compared to paired PBS controls. Moreover, the article concludes that such AGE product formation is greater in either fresh dialysis fluid or in dialysate which had been removed from patients immediately after installation, than in dialysates which had remained for longer periods in the peritoneal cavity. The formation of protein-derived fluorescence has been used as a marker of AGE product formation. The article further concludes that results suggest either that conventional peritoneal dialysis fluid contains a factor (or factors) which promotes AGE product formation, and that its concentration diminishes during dialysis, or that the concentration of an inhibitor of the reaction increases in the dialysate during dialysis. In the article it is mentioned that glycation of peritoneal membrane proteins may be involved in the etiology of ultrafiltration failure in CAPD and should the Maillard reaction prove to be relevant to the etiology of ultrafiltration failure, it may be possible to include inhibitors of the reaction in the dialysis fluid, such as aminoguanidine.

WO 93/09820, included herein in its entirety by reference, discloses a peritoneal dialysis solution containing glucose or glucose-like compounds, such as glucose polymers. The disclosed solution is sterilised before use. During sterilisation, the glucose component is sterilized separately from the remaining components at a high concentration of glucose, over 20%, and at a low pH. After sterilisation and preferably shortly before use, the components are mixed to form the final, ready-made peritoneal solution to be installed into the abdomen of the patient. The final solution has a pH of about 6.2–6.5.

Separate sterilization of the concentrated glucose component as described in WO 93/09820 results in a ready-made peritoneal dialysis solution having less break-down products from glucose as compared to a conventional peritoneal dialysis solution.

DISCLOSURE OF THE INVENTION

It could be expected that all peritoneal dialysis solutions comprising glucose should induce AGE formation.

However, it has unexpectedly been discovered that the peritoneal dialysis solution according to WO 93/09820 does not result in formation of AGE products in the same extent as conventional peritoneal dialysis solution. Consequently, a peritoneal dialysis solution according to WO 93/09820 can advantageously be used in patients where formation of AGE products is of importance, such as diabetic patients. Such use will avoid AGE related complications, such as vascular damage, dyslipidaemia and beta-2-microglobuline amyloidosis. Consequently, such use constitutes the second medical use of said peritoneal dialysis solution.

Further features and advantages of the invention will be described in more details below with reference to the appended drawings.

SHORT DESCRIPTION OF THE DRAWINGS

FIG. 1 is a diagram over incubation of two PD solutions and the resultant glycation.

FIG. 2 is a diagram over incubation of the same two PD solutions as in FIG. 1 and the resultant fluorescence generation.

DETAILED DESCRIPTION OF THE INVENTION

Experiments have shown that a peritoneal dialysis (PD) solution according to WO 93/09820, in the following refered to as the PD-BIO solution, results in less formation of late Maillard products during peritoneal dialysis.

FIG. 1 is a diagram according to which a standard PD solution and a PD-BIO solution according to WO 93/09820 are compared.

The standard PD solutions had the following approximate composition in mmol/l: sodium 135, potassium 2, calcium 1,5, magnesium 0,5 and lactate 35. The final glucose concentration was 1,5%. The standard PD solution was comprised in a two litre bag and was sterilised by autoclaving the entire bag. The pH was about 5,5.

The PD-BIO solution had the same final composition. It was comprised in a two litre bag having two separate compartments, one small, upper compartment enclosing only glucose at a concentration of about 50% and at a pH of about 3,2, and a larger, lower compartment enclosing the remaining components at a pH of about 6,7. The bag was autoclaved in this condition. Shortly before use, a frangible pin was broken whereby communication was established between the two compartments and the content of the upper compartment, glucose, was transported to the lower compartment by gravity, thereby forming the final PD solution having a pH of about 6,3.

The samples were buffered to pH 7,4 by the addition of sodium phosphate buffer to a final concentration of 50 mmol/l and was then spiked with HSA (human serum albumin) to an approximate concentration of 1 g/l.

The diagram in FIG. 1 discloses the glycation of the above-mentioned two solutions having a final glucose concentration of 1,5%. As can be seen from the diagram, there is substantially no difference in the glycation rates between the two solutions.

In FIG. 2, the same PD solutions as in FIG. 1 are shown relative to protein fluorescence generation, reflecting AGE formation according to the method described in the above-mentioned article "In vitro formation of advanced glycation end products in peritoneal dialysis fluid". As can clearly be seen, the standard PD fluid has a markedly higher generation of protein fluorescence, compared to the PD-BIO solution.

It is known that pyrraline is a marker for the presence of AGE products. As shown in table I below, the formation of pyrraline was measured for three different solutions, the PD-BIO solution, a conventional PD solution GAMBROSOL and a sterile filtered solution of the same composition as the GAMBROSOL solution, all having a glucose concentration of 4% and the same electrolyte composition as give above.

The samples were incubated for 16 hours or 7 days, at 37° C. under sterile conditions with human serum albumin (A) at a concentration of 40 g/l and without or with addition of 400 mmol/l glucose (G).

TABLE I

| | | pyrralline | |
|---|---|---|---|
| sample | incubation time | µg/g protein | pmol/mg protein |
| PD-BIO | | | |
| 16-A | 16 h | 17 | 67 |
| 7-A | 7 days | 22 | 88 |
| 16-GA | 16 h | 19 | 74 |
| 7-GA | 7 days | 23 | 89 |
| GAMBROSOL | | | |
| 16-A | 16 h | 25 | 97 |
| 7-A | 7 days | 75 | 294 |
| 16-GA | 16 h | 24 | 94 |
| 7-GA | 7 days | 65 | 257 |

TABLE I-continued

| | | pyrralline | |
|---|---|---|---|
| sample | incubation time | µg/g protein | pmol/mg protein |
| Sterile filtered | | | |
| 16-A | 16 h | 17 | 66 |
| 7-A | 7 days | 16 | 65 |
| 16-GA | 16 h | 16 | 63 |
| 7-GA | 7 days | 22 | 86 |

As can be seen from table I, the formation of pyrraline increased by a factor 3 between the 16 hour, incubation and the 7 day inhibation for the GAMBROSOL solution, but was substantially unchanged for the PD-BIO solution and the filtered GAMBROSOL solution.

Although not intended to be limited by any particular theory or hypothesis, it is believed that the above-mentioned data is indicative of the fact that conventional PD solutions sterilised in autoclaves in the final mixed composition, form degradation products of glucose acting as promoters for AGE formation. By the sterilisation method used in the PD-BIO solution, the concentration of such promoters is substantially reduced. This theory seems to be confirmed by the fact that sterile filtered PD solutions of the same composition as the GAMBROSOL solution and the PD-BIO solution do not substantially form pyrraline, as shown in table I.

In table II there is also shown the formation of fructose lysine and pentosidine after 7 days incubation. There seems to be no difference between the three solutions in this regard. Fructose lysine and pentosidine are also markers for AGE products. The conditions were the same as for table I.

TABLE II

| | fructose lysine | | pentosidine | |
|---|---|---|---|---|
| sample | nmol/mg HSA | mmol/mol HSA | pmol/mg HSA | mmol/mol HSA |
| PD-BIO | | | | |
| 7-GA | 79.0 | 5270 | 9.2 | 0.61 |
| 7-A | 35.9 | 2390 | 9.5 | 0.63 |
| GAMBROSOL | | | | |
| 7-GA | 77.6 | 5170 | 10.5 | 0.70 |
| 7-A | 31.2 | 2080 | 9.6 | 0.64 |
| sterile filtered | | | | |
| 7-GA | 73.6 | 4910 | 9.4 | 0.63 |
| 7-A | 36.5 | 2430 | 9.1 | 0.61 |

In order to find out which components in the peritoneal dialysis solution that are responsible for the AGE formation, a series of experiments were carried out, where a sterile filtered PD solution according to the above specifications were used. To the samples of the solution were added human serum albumin at 40 mg/ml as the target protein for AGE formation. In the different samples were added glucose degradation products in different amounts typically found in heat sterilised conventional peritoneal dialysis fluids. The samples were incubated over 0, 1, 10 or 30 days and the AGE formation was measured by fluorescence measurements as in FIG. 2. The results appear from table III below.

TABLE III

|  | t0 | t1 | t10 | t30 |
|---|---|---|---|---|
| Sterile filtered fluid | 150 | 154 | 169 | 196 |
| addition of acetaldehyde |  |  |  |  |
| 420 μmol | 160 | 169 | 177 | 198 |
| 1573 μmol | 166 | 173 | 188 | 218 |
| addition of formaldehyde |  |  |  |  |
| 15 μmol | 164 | 171 | 179 | 197 |
| 44 μmol | 165 | 171 | 181 | 201 |
| addition of methylglyoxal |  |  |  |  |
| 23 μmol | 162 | 165 | 162 | 194 |
| 164 μmol | 154 | 177 | 262 | 295 |
| addition of 5-HMF |  |  |  |  |
| 30 μmol | 157 | 156 | 164 | 193 |
| 1355 μmol | 157 | 156 | 176 | 219 |
| Autoclaved PD fluid | 160 | 217 | 318 | 371 |

As appears from table III, there seems to be a clear correlation between autoclaved PD fluids (GAMBROSOL) and AGE product formation as indicated by fluorescence. It seems that methylglyoxal also mediates AGE product formation, while the other substances do not seem to have much influence on such production in the used concentrations.

It is known that dicarbonyl compounds and specifically 3-deoxyglycosone, 3-DG, are formed during heat sterilisation of peritoneal dialysis solutions as a glucose degradation product. 3-DG is known to be a potent cross-linker. 3-DG is a highly reactive dicarbonyl intermediate, of the Maillard reactions and a precursor of the advanced glycosylation end products, AGEs, such as pyrraline. The production of 3-DG normally starts from glucose which forms a Schiffs base after reaction with the amino group of a protein. The next step in the Maillard reactions is rearrangement to Amadori products which than in the late Maillard reactions split to form 3-DG. However, 3-DG has also been suggested as a possible intermediate in the degradation of carbohydrates by acids to 2-furaldehyde. If this is possible, 3-DG could appear in fresh fluid for peritoneal dialysis as a glucose degradation product. We have found that dicarbonyl compounds are suppressed at least tenfold in the PD-BIO solution compared to the GAMBROSOL solution.

The above-mentioned data is given for solutions intended to be used for peritoneal dialysis. When such solutions are installed into a patient undergoing peritoneal dialysis treatment, the solution comes into contact with a great number of different proteins prevailing in the peritoneal cavity. Moreover, the solution is diluted with solution already present in the abdominal cavity. Finally, an exchange of electrolytes and molecules take place inside the cavity and notably with the blood through the peritoneal membrane.

During the exposure of the peritoneal cavity to PD solutions having an unphysiologically high concentration of glucose, it is likely that proteins present in the cavity undergo similar reactions as seen in the above examples. Such altered proteins are transported from the abdominal cavity via the peritoneal membrane to the blood and to the rest of the body. Moreover, any precursors or promoters of AGE products can be transported through the periotoneal membrane into the blood.

By using a PD solution having a low concentration of promoters of late stage advanced glycosylation end products, it is likely that adverse effects on the peritoneal membrane can be avoided as well as other complications associated with the generation of AGE products.

What is claimed is:

1. A method for the peritoneal dialysis of a patient susceptible to complications from advanced glycosylation end products comprising preparing a peritoneal dialysis solution by sterilizing a substantially pure glucose solution having a concentration of greater than about 20%, separately preparing a substantially glucose-free composition, and mixing said substantially pure sterilized glucose solution in said substantially glucose-free composition, to produce a solution having a reduced formation of said advanced glycosylation end products.

2. The method of claim 1, wherein said patient comprises a diabetic patient.

3. The method of claim 2, wherein said substantially pure sterilized glucose polymer solution has a concentration of greater than about 40%.

4. A method for the peritoneal dialysis of a patient susceptible to complications from advanced glycosylation end products comprising preparing a peritoneal dialysis solution by filter sterilizing a substantially pure glucose solution, separately preparing a substantially glucose-free composition, and mixing said substantially pure filter sterilized glucose solution in said substantially glucose-free composition to produce a solution having a reduced formation of said advanced glycosylation end products.

5. The method of claim 4, wherein said patient comprises a diabetic patient.

* * * * *

What is claimed is:

1. A method for the peritoneal dialysis of a patient susceptible to complications from advanced glycosylation end products comprising preparing a peritoneal dialysis solution by sterilizing a substantially pure glucose solution having a concentration of greater than about 20%, separately preparing a substantially glucose-free composition, and mixing said substantially pure sterilized glucose solution in said substantially glucose-free composition, to produce a solution having a reduced formation of said advanced glycosylation end products.

2. The method of claim 1, wherein said patient comprises a diabetic patient.

3. The method of claim 2, wherein said substantially pure sterilized glucose polymer solution has a concentration of greater than about 40%.

4. A method for the peritoneal dialysis of a patient susceptible to complications from advanced glycosylation end products comprising preparing a peritoneal dialysis solution by filter sterilizing a substantially pure glucose solution, separately preparing a substantially glucose-free composition, and mixing said substantially pure filter sterilized glucose solution in said substantially glucose-free composition to produce a solution having a reduced formation of said advanced glycosylation end products.

5. The method of claim 4, wherein said patient comprises a diabetic patient.

* * * * *

UNITED STATES PATENT AND TRADEMARK OFFICE
CERTIFICATE OF CORRECTION

PATENT NO. : 6,241,943 B1
APPLICATION NO. : 09/125470
DATED : June 5, 2001
INVENTOR(S) : Wiselander et al.

It is certified that error appears in the above-identified patent and that said Letters Patent is hereby corrected as shown below:

Delete title page and substitute therefore the attached title page.

Delete drawing and substitute therefor the attached drawing sheet.

Delete column 1-6 of the specification and substitute therefor columns 1-8 as per the attached new specification.

This certificate supersedes Certificate of Correction issued July 13, 2004 and September 21, 2004.

Signed and Sealed this

Nineteenth Day of December, 2006

JON W. DUDAS
*Director of the United States Patent and Trademark Office*

(12) United States Patent
Wieslander et al.

(10) Patent No.: US 6,241,943 B1
(45) Date of Patent: Jun. 5, 2001

(54) USE OF A SOLUTION COMPRISING GLUCOSE FOR PERITONEAL DIALYSIS HAVING REDUCED FORMATION OF AGE PRODUCTS

(75) Inventors: Anders Wieslander, Lund; Gunita Forsbäck, Löddeköpinge; Torbjörn Linden, Linderöd, all of (SE); Reinhold Deppisch, Hechingen; Thomas Henle, Freising, both of (DE); Anne Dawnay, London (GB)

(73) Assignee: Gambro AB (SE)

(*) Notice: Subject to any disclaimer, the term of this patent is extended or adjusted under 35 U.S.C. 154(b) by 0 days.

(21) Appl. No.: 09/125,470

(22) PCT Filed: Feb. 19, 1997

(86) PCT No.: PCT/SE97/00272

§ 371 Date: Dec. 1, 1998

§ 102(e) Date: Dec. 1, 1998

(87) PCT Pub. No.: WO97/30694

PCT Pub. Date: Aug. 28, 1997

(30) Foreign Application Priority Data

Feb. 20, 1996 (SE) .................................. 9600631

(51) Int. Cl.[7] ............................................. A61L 2/00
(52) U.S. Cl. ........................... 422/1; 422/25; 422/40; 422/41; 422/256; 604/28; 604/29; 604/408; 604/409; 604/410
(58) Field of Search ................................... 422/1, 25, 40, 422/41, 256; 604/408–410, 28, 29

(56) References Cited

U.S. PATENT DOCUMENTS

| | | | |
|---|---|---|---|
| 5,312,547 | * | 5/1994 | Kruger et al. ................. 210/317 |
| 5,536,469 | * | 7/1996 | Jonsson et al. .................. 422/1 |
| 5,643,201 | * | 7/1997 | Peabody et al. ................ 604/31 |

* cited by examiner

Primary Examiner—Krisanne Thornton
(74) Attorney, Agent, or Firm—Lerner, David, Littenberg, Krumholz & Mentlik, LLP

(57) ABSTRACT

Use of a solution comprising glucose for peritoneal dialysis, in which the glucose portion is sterilised separately from the remaining components at a high glucose concentration above about 20% and mixed after sterilisation, substantially according to WO 93/09820. The solution has a reduced formation of advanced glycosylation end products and the use is indicated for diabetic uremic patients.

5 Claims, 1 Drawing Sheet

USE OF A SOLUTION COMPRISING GLUCOSE FOR PERITONEAL DIALYSIS HAVING REDUCED FORMATION OF AGE PRODUCTS

FIELD OF THE INVENTION

The present invention relates to the use of a solution comprising glucose. More particularly, the present invention relates to glucose solution which are intended for peritoneal dialysis, and having reduced formation of AGE products.

BACKGROUND OF THE INVENTION

Peritoneal dialysis is a treatment which is performed when the renal capacity of a patient's kidney is impaired. A peritoneal dialysis solution is installed in the patients abdominal cavity by means of a catheter, and exchange between the blood and the dialysis solution takes place across the peritoneal membrane, whereupon the dialysis solution is then drained. In order to obtain fluid removal, the dialysis solution comprises an osmotic agent, usually glucose.

It is known that mixing glucose with amino-containing compounds results in a series of non-enzymatic reactions called Maillard reactions, resulting in advanced glucosylation end products. Reference in this regard is made to PCT Patent Nos. WO 93/13421 and WO 95/30153. It is believed that advanced glucosylation end products are involved in the ageing process of mammals.

Advanced glycosylation end products, or AGEs, are known as one candidate to cause diabetic complications. These products are derived from non-enzymatic glycosylation of long-lived proteins that are further modified by the advanced stage of the Maillard reactions, resulting in the formation of glucose-derived cross-links with a brown or fluorescent property. These products increase the vascular permeability through several mechanisms, such as the disturbed integration of basement membrane components due to the cross-linking of proteins, the endothelial cell reaction to the AGE receptor-mediated cytokine release from macrophage, or the occupancy of endothelial cell AGE receptors.

The rise of AGEs is also associated with a variety of tissue disorders, including vascular damage, dyslipidemia and beta-2-microglobuline amyloidosis. Moreover, it has been suggested that elevated AGE levels may mediate the suppression of certain normal host defense mechanisms, such as inhibition of certain bacteriocidal activites.

Advanced glycation has also been implicated in the pathology of Alzheimer's disease.

It has also been suggested that AGE generation is enhanced by an increased oxidative stress associated with uremia.

Formation of advanced glycosylation end products, AGEs, in connection with peritoneal dialysis has been suggested in the article "In vitro formation of advanced glycation end products in peritoneal dialysis fluid" by Edmund J. Lamb, William R. Cattell and Anne B. St. H. Dawney, published in Kidney International, Vol. 47 (1995) pages 1768–1774 (the expressions "glycosylated" and "glycated" are used interchangeably for the same property). This article investigates peritoneal dialysis solutions of conventional compositions in which all components are heat sterilized together as a single solution. The article suggests that such conventional peritoneal dialysis fluid does not contain inhibitors or promoters of the early Maillard reaction other than glucose. The article states that late Maillard reaction products are formed to a higher extent in conventional peritoneal dialysis solutions compared to paired PBS controls. Moreover, the article concludes that such AGE product formation is greater in either fresh dialysis fluid or in dialysate which had been removed from patients immediately after installation, than in dialysates which had remained for longer periods in the peritoneal cavity. The formation of protein-derived fluorescence has been used as a marker of AGE product formation. The article further concludes that results suggest either that conventional peritoneal dialysis fluid contains a factor (or factors) which promotes AGE product formation, and that its concentration diminishes during dialysis, or that the concentration of an inhibitor of the reaction increases in the dialysate during dialysis. In the article it is mentioned that glycation of peritoneal membrane proteins may be involved in the etiology of ultrafiltration failure in CAPD and should the Maillard reaction prove to be relevant to the etiology of ultrafiltration failure, it may be possible to include inhibitors of the reaction in the dialysis fluid, such as aminoguanidine.

PCT Patent No. WO 93/09820, the disclosure of which is incorporated herein by reference thereto, discloses a peritoneal dialysis solution containing glucose or glucose-like compounds, such as glucose polymers. The disclosed solution is sterilised before use. During sterilisation, the glucose component is sterilized separately from the remaining components at a high concentration of glucose, over 20%, and at a low pH. After sterilisation and preferably shortly before use, the components are mixed to form the final, ready-made peritoneal solution to be installed into the abdomen of the patient. The final solution has a pH of about 6.2–6.5.

Separate sterilization of the concentrated glucose component as described in PCT Patent No. WO 93/09820 results in a ready-made peritoneal dialysis solution having less breakdown products from glucose as compared to a conventional peritoneal dialysis solution.

SUMMARY OF THE INVENTION

It could be expected that all peritoneal dialysis solutions comprising glucose should induce AGE formation.

However, it has unexpectedly been discovered that the peritoneal dialysis solution according to WO 93/09820 does not result in formation of AGE products to the same extent as conventional peritoneal dialysis solution. Consequently, a peritoneal dialysis solution according to PCT Patent No. WO 93/09820 can advantageously be used in patients where formation of AGE products is of importance, such as diabetic patients. Such use will avoid AGE related complications, such as vascular damage, dyslipidaemia and beta-2-microglobuline amyloidosis. Consequently, such use constitutes the second medical use of said peritoneal dialysis solution.

In accordance with the present invention, these objects have been accomplished by discovery of a method for the preparation of a peritoneal dialysis solution which comprises sterilizing a substantially pure glucose solution having a concentration of greater than about 20%, separately preparing a substantially glucose-free composition, and mixing the substantially pure sterilized glucose solution and the substantially glucose-free composition, the mixture having a reduced formation of advanced glycosylation end products. In a preferred embodiment the substantially pure sterilized glucose solution has a concentration of greater than about 40%.

In accordance with another embodiment of the method of the present invention, the method for preparation of a peritoneal dialysis solution comprises preparing a substantially pure sterilized glucose polymer solution having a concentration of greater than about 20%, separately preparing a substantially glucose-free composition, and mixing together the substantially pure sterilized glucose polymer solution and the substantially glucose-polymer-free composition so as to prepare a solution having reduced formulation of advanced glcosylation end products. Preferably, the substantially pure sterilized glucose polymer solution has a concentration of greater than about 40%.

In accordance with another embodiment of the method of the present invention, the method comprises preparation of a peritoneal dialysis solution comprising filter sterilizing a substantially pure glucose solution, separately preparing a substantially glucose-free composition, and mixing the substantially pure filter sterilized glucose solution and the substantially glucose-free composition to produce a solution having a reduced formation of advanced glycosylation end product.

In accordance with another embodiment of the method of the present invention, the method includes preparation of a peritoneal dialysis solution comprising sterilizing a substantially pure glucose solution having a concentration greater than about 20%, and using the substantially pure sterilized glucose solution to produce a peritoneal dialysis solution having a reduced formation of advanced glycosylation end products for treatment of age-related diseases.

According to the present invention, a peritoneal dialysis solution has been discovered which comprises substantially pure sterilized glucose having a concentration of greater than about 20% and a substantially glucose-free composition, the substantially pure sterilized glucose solution and the substantially glucose-free composition being mixed together for use in peritoneal dialysis and having a reduced formation of advanced glycosylation end products. Preferably, the glucose comprises a glucose polymer. In another embodiment, the substantially sterilized glucose solution comprises a substantially pure filter sterilized glucose solution.

BRIEF DESCRIPTION OF THE DRAWINGS

The subject matter of the present invention can be more fully appreciated with reference to the following detailed description, which, in turn, refers to the drawings in which.

DETAILED DESCRIPTION

Experiments have shown that a peritoneal dialysis (PD) solution according to PCT Patent No. WO 93/09820, hereafter referred to as the PD-BIO solution, results in less formation of late Maillard products during peritoneal dialysis.

Figure 1:
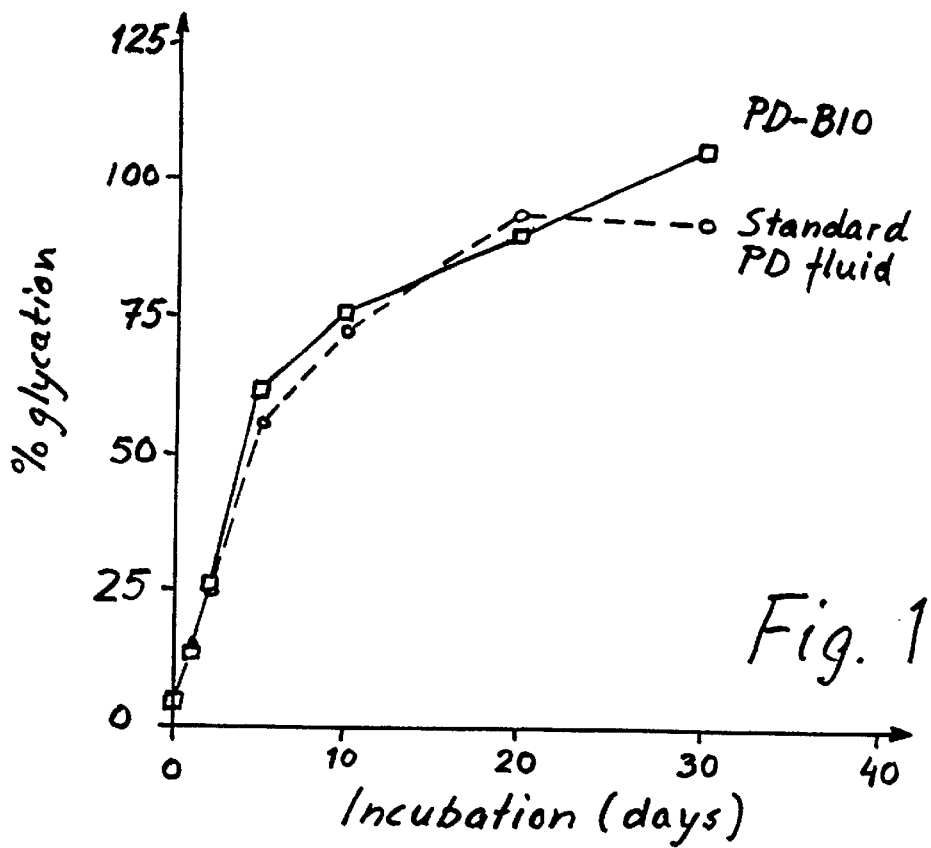
FIG. 1 is a graphical representation showing incubation of two PD solutions against percentage glycation.

FIG. 1 is a diagram according to which a standard PD solution and a PD-BIO solution according to WO 93/09820 are compared.

The standard PD solutions had the following approximate composition in mmol/l: sodium 135, potassium 2, calcium 1.5, magnesium 0.5 and lactate 35. The final glucose concentration was 1.5%. The standard PD solution was comprised in a two liter bag and was sterilised by autoclaving the entire bag. The pH was about 5.5.

The PD-BIO solution had the same final composition. It was comprised in a two liter bag having two separate compartments, one small, upper compartment enclosing only glucose at a concentration of about 50% and at a pH of about 3.2, and a larger, lower compartment enclosing the remaining components at a pH of about 6.7. The bag was autoclaved in this condition. Shortly before use, a frangible pin was broken whereby communication was established between the two compartments and the content of the upper compartment, namely glucose, was transported to the lower compartment by gravity, thereby forming the final PD solution having a pH of about 6.3.

The samples were buffered to pH 7.4 by the addition of sodium phosphate buffer to a final concentration of 50 mmol/l and was then spiked with HSA (human serum albumin) to an approximate concentration of 1 g/l.

The diagram in FIG. 1 discloses the glycation of the above-mentioned two solutions having a final glucose concentration of 1.5%. As can be seen from the diagram, there is substantially no difference in the glycation rates between the two solutions.

Figure 2:
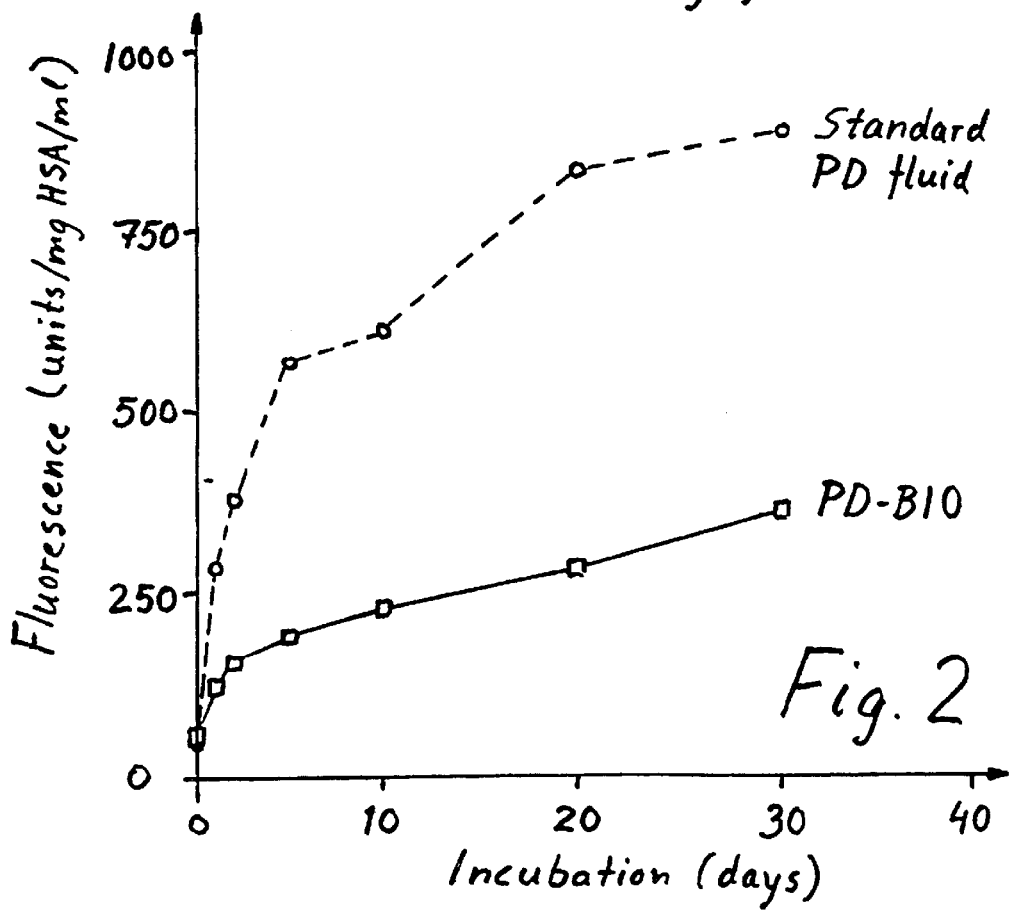
FIG. 2 is a graphical representation showing incubation of the same two PD solutions shown in FIG. 1, and the resultant fluorescence generation thereagainst.
Figure 1:
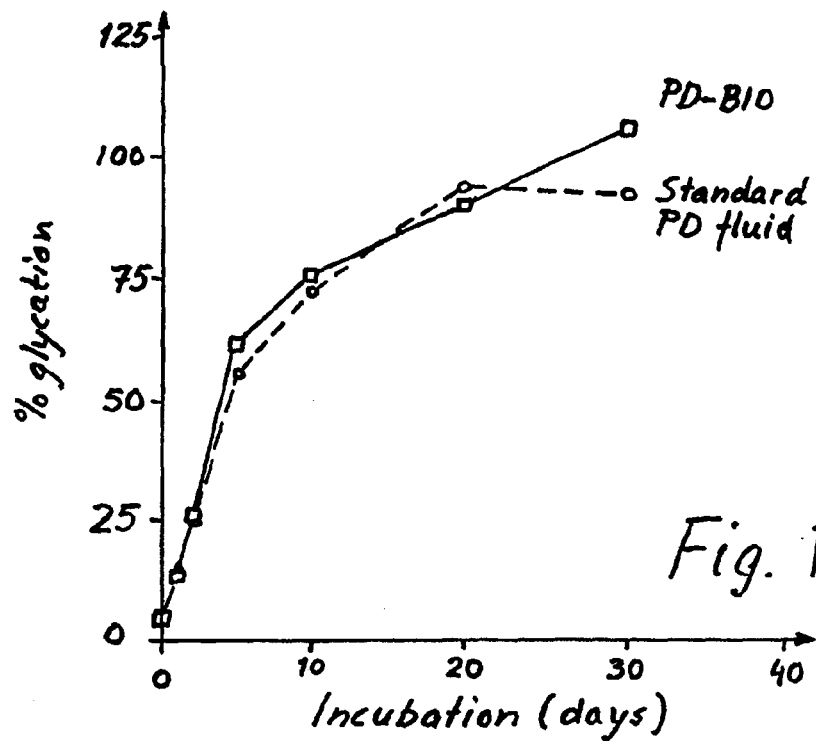
Figure 2:
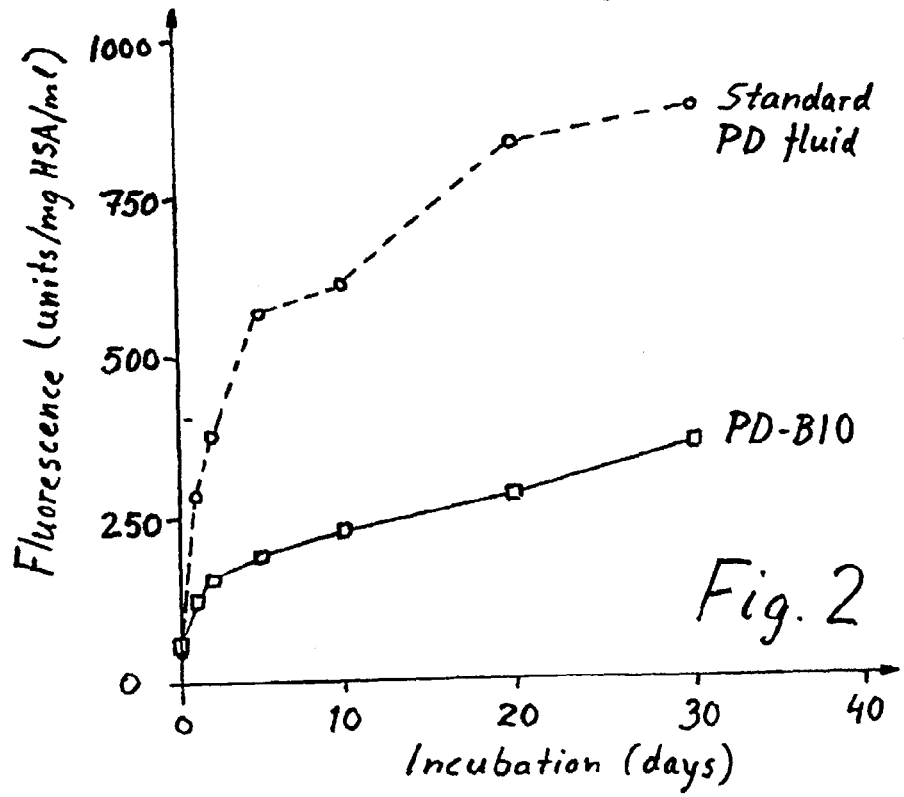
Figure 1:
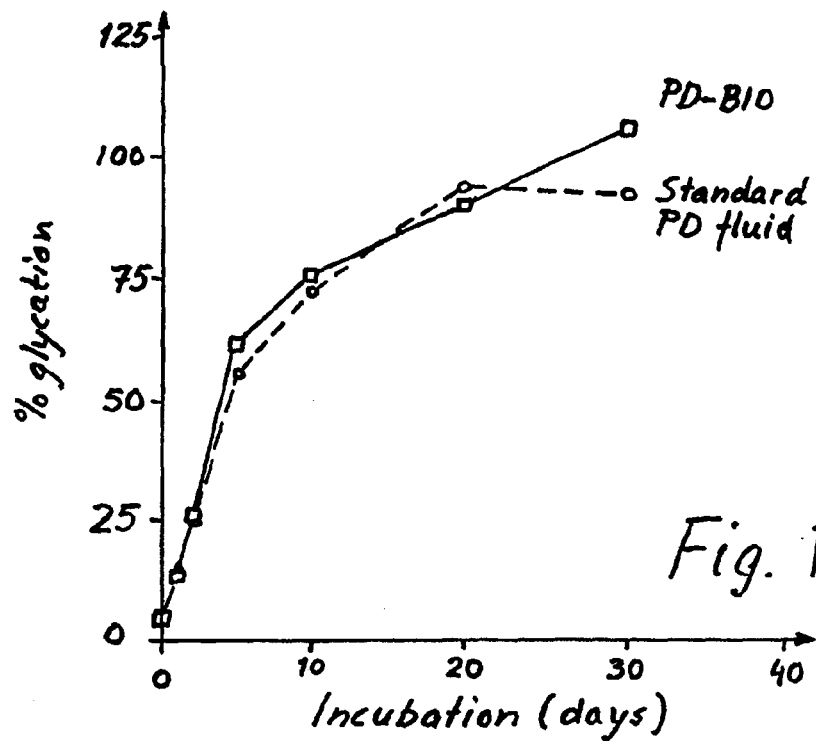
Figure 2:
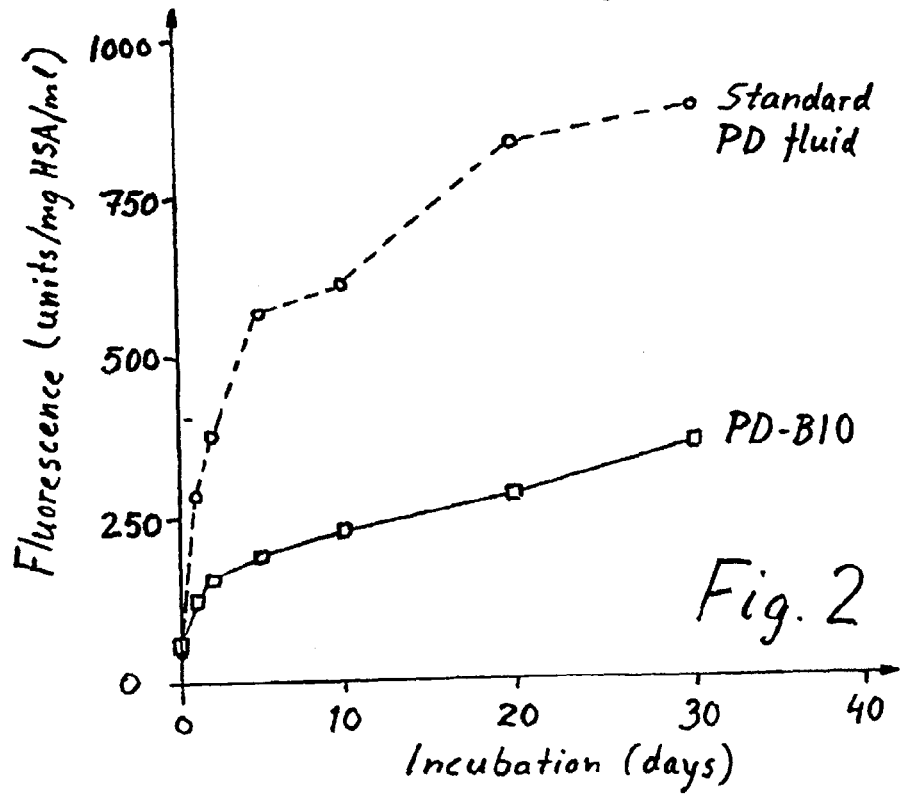
Figure 1:
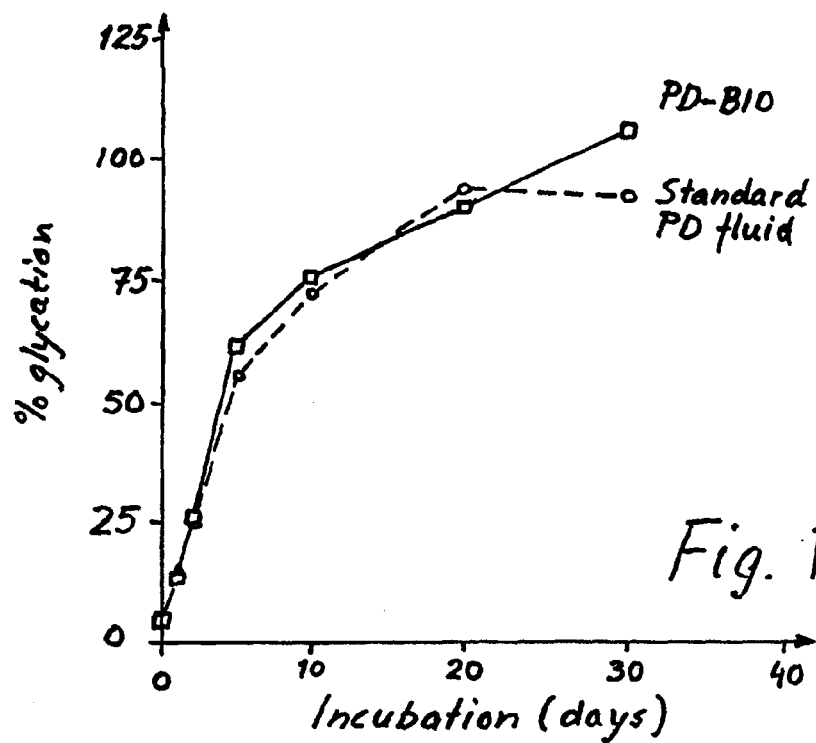
Figure 2:
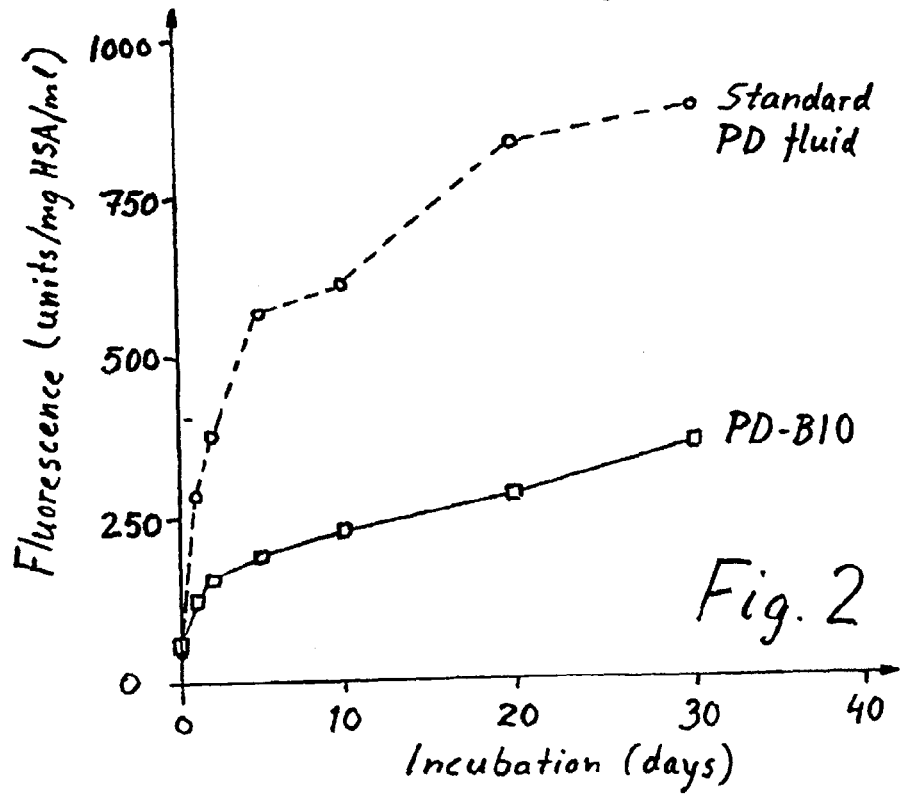
Figure 1:
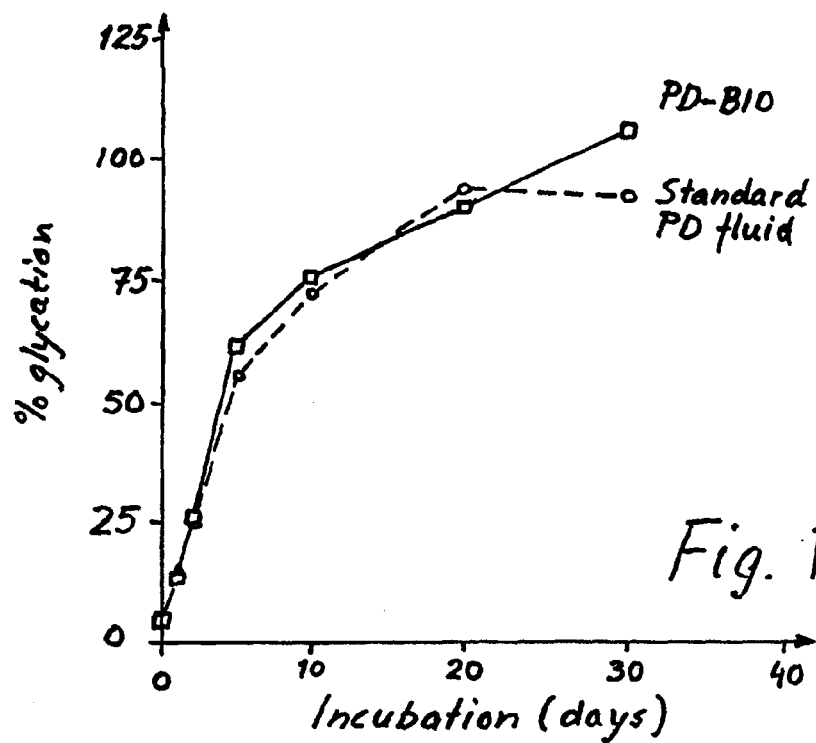
Figure 2:
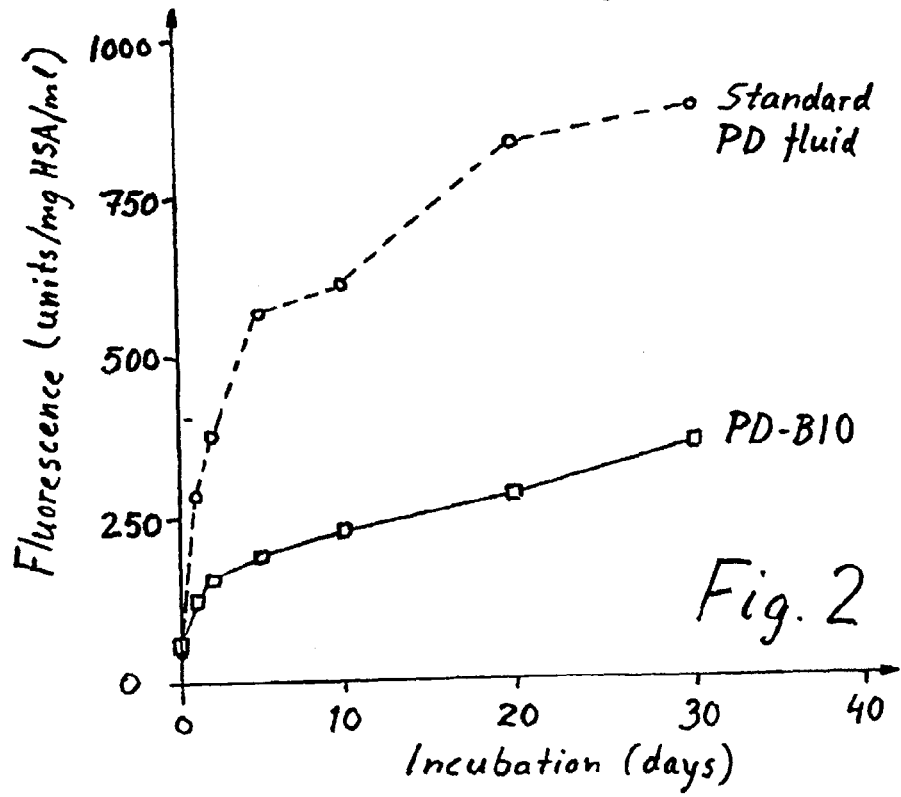

In FIG. 2, the same PD solutions as in FIG. 1 are shown relative to protein fluorescence generation, reflecting AGE formation according to the method described in the above-mentioned article "In vitro formation of advanced glycation end products in peritoneal dialysis fluid." As can clearly be seen, the standard PD fluid has a markedly higher generation of protein fluorescence, compared to the PD-BIO solution.

It is known that pyrraline is a marker for the presence of AGE products. As shown in table I below, the formation of pyrraline was measured for three different solutions, the PD-BIO solution, a conventional PD solution GAMBROSOL and a sterile filtered solution of the same composition as the GAMBROSOL solution, all having a glucose concentration of 4% and the same electrolyte composition as give above.

The samples were incubated for 16 hours or 7 days, at 37° C. under sterile conditions with human serum albumin (A) at a concentration of 40 g/l and without or with addition of 400 mmol/l glucose (G).

TABLE I

| | | pyrraline | |
|---|---|---|---|
| sample | incubation time | µg/g protein | pmol/mg protein |
| PD-BIO | | | |
| 16-A | 16 h | 17 | 67 |
| 7-A | 7 days | 22 | 88 |
| 16-GA | 16 h | 19 | 74 |
| 7-GA | 7 days | 23 | 89 |
| GAMBROSOL | | | |
| 16-A | 16 h | 25 | 97 |
| 7-A | 7 days | 75 | 294 |
| 16-GA | 16 h | 24 | 94 |
| 7-GA | 7 days | 65 | 257 |
| Sterile filtered | | | |
| 16-A | 16 h | 17 | 66 |
| 7-A | 7 days | 16 | 65 |
| 16-GA | 16 h | 16 | 63 |
| 7-GA | 7 days | 22 | 86 |

As can be seen from table I, the formation of pyrraline increased by a factor of 3 between the 16 hour incubation and the 7 day inhibition for the GAMBROSOL solution, but was substantially unchanged for the PD-BIO solution and the filtered GAMBROSOL solution.

Although not intended to be limited by any particular theory or hypothesis, it is believed that the above-mentioned data is indicative of the fact that conventional PD solutions sterilised in autoclaves in the final mixed composition, form degradation products of glucose acting as promoters for AGE formation. By the sterilisation method used in the PD-BIO solution, the concentration of such promoters is substantially reduced. This theory seems to be confirmed by the fact that sterile filtered PD solutions of the same composition as the GAMBROSOL solution and the PD-BIO solution do not substantially form pyrraline, as shown in table I.

In table II there is also shown the formation of fructose lysine and pentosidine after 7 days incubation. There seems to be no difference between the three solutions in this regard. Fructose lysine and pentosidine are also markers for AGE products. The conditions were the same as for table I.

TABLE II

| sample | fructose lysine | | pentosidine | |
| --- | --- | --- | --- | --- |
| | nmol/mg HSA | mmol/mol HSA | pmol/mg HSA | mmol/mol HSA |
| PD-BIO | | | | |
| 7-GA | 79.0 | 5270 | 9.2 | 0.61 |
| 7-A | 35.9 | 2390 | 9.5 | 0.63 |
| GAMBROSOL | | | | |
| 7-GA | 77.6 | 5170 | 10.5 | 0.70 |
| 7-A | 31.2 | 2080 | 9.6 | 0.64 |
| sterile filtered | | | | |
| 7-GA | 73.6 | 4910 | 9.4 | 0.63 |
| 7-A | 36.5 | 2430 | 9.1 | 0.61 |

In order to find out which components in the peritoneal dialysis solution are responsible for the AGE formation, a series of experiments were carried out, in which a sterile filtered PD solution according to the above specification was used. To the samples of the solution were added human serum albumin at 40 mg/ml as the target protein for AGE formation. In the different samples were added glucose degradation products in different amounts typically found in heat sterilised conventional peritoneal dialysis fluids. The samples were incubated over 0, 1, 10 or 30 days and the AGE formation was measured by fluorescence measurements as in FIG. 2. The results appear from table III below.

TABLE III

| | t0 | t1 | t10 | t30 |
| --- | --- | --- | --- | --- |
| Sterile filtered fluid | 150 | 154 | 169 | 196 |
| addition of acetaldehyde | | | | |
| 420 µmol | 160 | 169 | 177 | 198 |
| 1573 µmol | 166 | 173 | 188 | 218 |
| addition of formaldehyde | | | | |
| 15 µmol | 164 | 171 | 179 | 197 |
| 44 µmol | 165 | 171 | 181 | 201 |
| addition of methylglyoxal | | | | |
| 23 µmol | 162 | 165 | 162 | 194 |
| 164 µmol | 154 | 177 | 262 | 295 |

TABLE III-continued

| | t0 | t1 | t10 | t30 |
| --- | --- | --- | --- | --- |
| addition of 5-HMF | | | | |
| 30 µmol | 157 | 156 | 164 | 193 |
| 1355 µmol | 157 | 156 | 176 | 219 |
| Autoclaved PD fluid | 160 | 217 | 318 | 371 |

As appears from table III, there seems to be a clear correlation between autoclaved PD fluids and AGE product formation as indicated by fluorescence. It appears that methylglyoxal also mediates AGE product formation, while the other substances do not seem to have much influence on such production in the used concentrations.

It is known that dicarbonyl compounds and specifically 3-deoxyglucosone, 3-DG, are formed during heat sterilisation of peritoneal dialysis solutions as a glucose degradation product. 3-DG is known to be a potent cross-linker. 3-DG is a highly reactive dicarbonyl intermediate of the Maillard reactions and a precursor of the advanced glycosylation end products, AGEs, such as pyrraline. The production of 3-DG normally starts from glucose which forms a Schiff's base after reaction with the amino group of a protein. The next step in the Maillard reactions is rearrangement to Amadori products which than in the late Maillard reactions split to form 3-DG. However, 3-DG has also been suggested as a possible intermediate in the degradation of carbohydrates by acids to 2-furaldehyde. If this is possible, 3-DG could appear in fresh fluid for peritoneal dialysis as a glucose degradation product. We have found that dicarbonyl compounds are suppressed at least tenfold in the PD-BIO solution compared to the GAMBROSOL solution.

The above-mentioned data is given for solutions intended to be used for peritoneal dialysis. When such solutions are installed into a patient undergoing peritoneal dialysis treatment, the solution comes into contact with a great number of different proteins prevailing in the peritoneal cavity. Moreover, the solution is diluted with solution already present in the abdominal cavity. Finally, an exchange of electrolytes and molecules take place inside the cavity and notably with the blood through the peritoneal membrane.

During the exposure of the peritoneal cavity to PD solutions having an unphysiologically high concentration of glucose, it is likely that proteins present in the cavity undergo similar reactions as seen in the above examples. Such altered proteins are transported from the abdominal cavity via the peritoneal membrane to the blood and to the rest of the body.

By using a PD solution having a low concentration of promoters of late stage advanced glycosylation end products, it is likely that adverse effects on the peritoneal membrane can be avoided as well as other complications associated with the generation of AGE products.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for the peritoneal dialysis of a patient susceptible to complications from advanced glycosylation end products comprising preparing a peritoneal dialysis solution by sterilizing a substantially pure glucose solution having a concentration of greater than about 20%, separately preparing a substantially glucose-free composition, and mixing said substantially pure sterilized glucose solution in said substantially glucose-free composition, to produce a solution having a reduced formation of said advanced glycosylation end products.

2. The method of claim 1, wherein said patient comprises a diabetic patient.

3. The method of claim 2, wherein said substantially pure sterilized glucose polymer solution has a concentration of greater than about 40%.

4. A method for the peritoneal dialysis of a patient susceptible to complications from advanced glycosylation end products comprising preparing a peritoneal dialysis solution by filter sterilizing a substantially pure glucose solution, separately preparing a substantially glucose-free composition, and mixing said substantially pure filter sterilized glucose solution in said substantially glucose-free composition to produce a solution having a reduced formation of said advanced glycosylation end products.

5. The method of claim 4, wherein said patient comprises a diabetic patient.

* * * * *

UNITED STATES PATENT AND TRADEMARK OFFICE
CERTIFICATE OF CORRECTION

PATENT NO. : 6,241,943 B1
APPLICATION NO. : 09/125470
DATED : June 5, 2001
INVENTOR(S) : Wiselander et al.

It is certified that error appears in the above-identified patent and that said Letters Patent is hereby corrected as shown below:

Delete title page and substitute therefore the attached title page.

Delete drawing and substitute therefor the attached drawing sheet.

Delete column 1-6 of the specification and substitute therefor columns 1-8 as per the attached new specification.

This certificate supersedes all previously issued Certificate of Corrections.

Signed and Sealed this

First Day of May, 2007

JON W. DUDAS
*Director of the United States Patent and Trademark Office*

(12) United States Patent
Wieslander et al.

(10) Patent No.: US 6,241,943 B1
(45) Date of Patent: Jun. 5, 2001

(54) USE OF A SOLUTION COMPRISING GLUCOSE FOR PERITONEAL DIALYSIS HAVING REDUCED FORMATION OF AGE PRODUCTS

(75) Inventors: Anders Wieslander, Lund; Gunilla Forsbäck, Löddeköpinge; Torbjörn Linden, Linderöd, all of (SE); Reinhold Deppisch, Hechingen; Thomas Henle, Freising, both of (DE); Anne Dawnay, London (GB)

(73) Assignee: Gambro AB (SE)

( * ) Notice: Subject to any disclaimer, the term of this patent is extended or adjusted under 35 U.S.C. 154(b) by 0 days.

(21) Appl. No.: 09/125,470

(22) PCT Filed: Feb. 19, 1997

(86) PCT No.: PCT/SE97/00272

§ 371 Date: Dec. 1, 1998

§ 102(e) Date: Dec. 1, 1998

(87) PCT Pub. No.: WO97/30694

PCT Pub. Date: Aug. 28, 1997

(30) Foreign Application Priority Data

Feb. 20, 1996 (SE) .................................... 9600631

(51) Int. Cl.[7] .................................................. A61L 2/00
(52) U.S. Cl. ............................ 422/1; 422/25; 422/40; 422/41; 422/256; 604/28; 604/29; 604/408; 604/409; 604/410
(58) Field of Search ..................... 422/1, 25, 40, 422/41, 256; 604/408–410, 28, 29

(56) References Cited

U.S. PATENT DOCUMENTS 5,312,547 * 5/1994 Kruger et al. ...................... 210/317
5,536,469 * 7/1996 Jonsson et al. ........................ 422/1
5,643,201 * 7/1997 Peabody et al. ..................... 604/31

FOREIGN PATENT DOCUMENTS

91/08008   6/1991  (WO).
93/09820   5/1993  (WO).
93/13421   7/1993  (WO).
95/30153  11/1995  (WO).

OTHER PUBLICATIONS

Edmund J. Lamb, William R. Cattell and Anne B. St. H. Dawney, "In vitro formation of advanced glycation end products in peritoneal dialysis fluid," *Kidney International*, vol. 47 (1995) pp. 1768–1774.

* cited by examiner

*Primary Examiner*—Krisanne Thornton
(74) *Attorney, Agent, or Firm*—Lerner, David, Littenberg, Krumholz & Mentlik, LLP

(57) ABSTRACT

Methods for preparing peritoneal dialysis solution are disclosed including sterilizing a substantially pure glucose solution having a concentration of greater than about 20%, separately preparing a substantially glucose-free composition, and mixing the substantially pure sterilized glucose solution and the substantially glucose-free composition so that the mixture has a reduced formation of advanced glycosylation products. Improved peritoneal dialysis solutions are also disclosed.

5 Claims, 1 Drawing Sheet

USE OF A SOLUTION COMPRISING GLUCOSE FOR PERITONEAL DIALYSIS HAVING REDUCED FORMATION OF AGE PRODUCTS

FIELD OF THE INVENTION

The present invention relates to the use of a solution comprising glucose. More particularly, the present invention relates to glucose solution which are intended for peritoneal dialysis, and having reduced formation of AGE products.

BACKGROUND OF THE INVENTION

Peritoneal dialysis is a treatment which is performed when the renal capacity of a patient's kidney is impaired. A peritoneal dialysis solution is installed in the patients abdominal cavity by means of a catheter, and exchange between the blood and the dialysis solution takes place across the peritoneal membrane, whereupon the dialysis solution is then drained. In order to obtain fluid removal, the dialysis solution comprises an osmotic agent, usually glucose.

It is known that mixing glucose with amino-containing compounds results in a series of non-enzymatic reactions called Maillard reactions, resulting in advanced glucosylation end products. Reference in this regard is made to PCT Patent Nos. WO 93/13421 and WO 95/30153. It is believed that advanced glucosylation end products are involved in the ageing process of mammals.

Advanced glycosylation end products, or AGEs, are known as one candidate to cause diabetic complications. These products are derived from non-enzymatic glycosylation of long-lived proteins that are further modified by the advanced stage of the Maillard reactions, resulting in the formation of glucose-derived cross-links with a brown or fluorescent property. These products increase the vascular permeability through several mechanisms, such as the disturbed integration of basement membrane components due to the cross-linking of proteins, the endothelial cell reaction to the AGE receptor-mediated cytokine release from macrophage, or the occupancy of endothelial cell AGE receptors.

The rise of AGEs is also associated with a variety of tissue disorders, including vascular damage, dyslipidemia and beta-2-microglobuline amyloidosis. Moreover, it has been suggested that elevated AGE levels may mediate the suppression of certain normal host defense mechanisms, such as inhibition of certain bacteriocidal activites.

Advanced glycation has also been implicated in the pathology of Alzheimer's disease.

It has also been suggested that AGE generation is enhanced by an increased oxidative stress associated with uremia.

Formation of advanced glycosylation end products, AGEs, in connection with peritoneal dialysis has been suggested in the article "In vitro formation of advanced glycation end products in peritoneal dialysis fluid" by Edmund J. Lamb, William R. Cattell and Anne B. St. H. Dawney, published in Kidney International, Vol. 47 (1995) pages 1768–1774 (the expressions "glycosylated" and "glycated" are used interchangeably for the same property). This article investigates peritoneal dialysis solutions of conventional compositions in which all components are heat sterilized together as a single solution. The article suggests that such conventional peritoneal dialysis fluid does not contain inhibitors or promoters of the early Maillard reaction other than glucose. The article states that late Maillard reaction products are formed to a higher extent in conventional peritoneal dialysis solutions compared to paired PBS controls. Moreover, the article concludes that such AGE product formation is greater in either fresh dialysis fluid or in dialysate which had been removed from patients immediately after installation, than in dialysates which had remained for longer periods in the peritoneal cavity. The formation of protein-derived fluorescence has been used as a marker of AGE product formation. The article further concludes that results suggest either that conventional peritoneal dialysis fluid contains a factor (or factors) which promotes AGE product formation, and that its concentration diminishes during dialysis, or that the concentration of an inhibitor of the reaction increases in the dialysate during dialysis. In the article it is mentioned that glycation of peritoneal membrane proteins may be involved in the etiology of ultrafiltration failure in CAPD and should the Maillard reaction prove to be relevant to the etiology of ultrafiltration failure, it may be possible to include inhibitors of the reaction in the dialysis fluid, such as aminoguanidine.

PCT Patent No. WO 93/09820, the disclosure of which is incorporated herein by reference thereto, discloses a peritoneal dialysis solution containing glucose or glucose-like compounds, such as glucose polymers. The disclosed solution is sterilised before use. During sterilisation, the glucose component is sterilized separately from the remaining components at a high concentration of glucose, over 20%, and at a low pH. After sterilisation and preferably shortly before use, the components are mixed to form the final, ready-made peritoneal solution to be installed into the abdomen of the patient. The final solution has a pH of about 6.2–6.5.

Separate sterilization of the concentrated glucose component as described in PCT Patent No. WO 93/09820 results in a ready-made peritoneal dialysis solution having less breakdown products from glucose as compared to a conventional peritoneal dialysis solution.

SUMMARY OF THE INVENTION

It could be expected that all peritoneal dialysis solutions comprising glucose should induce AGE formation.

However, it has unexpectedly been discovered that the peritoneal dialysis solution according to WO 93/09820 does not result in formation of AGE products to the same extent as conventional peritoneal dialysis solution. Consequently, a peritoneal dialysis solution according to PCT Patent No. WO 93/09820 can advantageously be used in patients where formation of AGE products is of importance, such as diabetic patients. Such use will avoid AGE related complications, such as vascular damage, dyslipidaemia and beta-2-microglobuline amyloidosis. Consequently, such use constitutes the second medical use of said peritoneal dialysis solution.

In accordance with the present invention, these objects have been accomplished by discovery of a method for the preparation of a peritoneal dialysis solution which comprises sterilizing a substantially pure glucose solution having a concentration of greater than about 20%, separately preparing a substantially glucose-free composition, and mixing the substantially pure sterilized glucose solution and the substantially glucose-free composition, the mixture having a reduced formation of advanced glycosylation end products. In a preferred embodiment the substantially pure sterilized glucose solution has a concentration of greater than about 40%.

In accordance with another embodiment of the method of the present invention, the method for preparation of a peritoneal dialysis solution comprises preparing a substantially pure sterilized glucose polymer solution having a concentration of greater than about 20%, separately preparing a substantially glucose-free composition, and mixing together the substantially pure sterilized glucose polymer solution and the substantially glucose-polymer-free composition so as to prepare a solution having reduced formulation of advanced glcosylation end products. Preferably, the substantially pure sterilized glucose polymer solution has a concentration of greater than about 40%.

In accordance with another embodiment of the method of the present invention, the method comprises preparation of a peritoneal dialysis solution comprising filter sterilizing a substantially pure glucose solution, separately preparing a substantially glucose-free composition, and mixing the substantially pure filter sterilized glucose solution and the substantially glucose-free composition to produce a solution having a reduced formation of advanced glycosylation end product.

In accordance with another embodiment of the method of the present invention, the method includes preparation of a peritoneal dialysis solution comprising sterilizing a substantially pure glucose solution having a concentration greater than about 20%, and using the substantially pure sterilized glucose solution to produce a peritoneal dialysis solution having a reduced formation of advanced glycosylation end products for treatment of age-related diseases.

According to the present invention, a peritoneal dialysis solution has been discovered which comprises substantially pure sterilized glucose having a concentration of greater than about 20% and a substantially glucose-free composition, the substantially pure sterilized glucose solution and the substantially glucose-free composition being mixed together for use in peritoneal dialysis and having a reduced formation of advanced glycosylation end products. Preferably, the glucose comprises a glucose polymer. In another embodiment, the substantially sterilized glucose solution comprises a substantially pure filter sterilized glucose solution.

BRIEF DESCRIPTION OF THE DRAWINGS

The subject matter of the present invention can be more fully appreciated with reference to the following detailed description, which, in turn, refers to the drawings in which:

FIG. 1 is a graphical representation showing incubation of two PD solutions against percentage glycation; and FIG. 2 is a graphical representation showing incubation of the same two PD solutions shown in FIG. 1, and the resultant fluorescence generation thereagainst.

DETAILED DESCRIPTION

Experiments have shown that a peritoneal dialysis (PD) solution according to PCT Patent No. WO 93/09820, hereafter referred to as the PD-BIO solution, results in less formation of late Maillard products during peritoneal dialysis.

FIG. 1 is a diagram according to which a standard PD solution and a PD-BIO solution according to WO 93/09820 are compared.

The standard PD solutions had the following approximate composition in mmol/l: sodium 135, potassium 2, calcium 1.5, magnesium 0.5 and lactate 35. The final glucose concentration was 1.5%. The standard PD solution was comprised in a two liter bag and was sterilised by autoclaving the entire bag. The pH was about 5.5.

The PD-BIO solution had the same final composition. It was comprised in a two liter bag having two separate compartments, one small, upper compartment enclosing only glucose at a concentration of about 50% and at a pH of about 3.2, and a larger, lower compartment enclosing the remaining components at a pH of about 6.7. The bag was autoclaved in this condition. Shortly before use, a frangible pin was broken whereby communication was established between the two compartments and the content of the upper compartment, namely glucose, was transported to the lower compartment by gravity, thereby forming the final PD solution having a pH of about 6.3.

The samples were buffered to pH 7.4 by the addition of sodium phosphate buffer to a final concentration of 50 mmol/l and was then spiked with HSA (human serum albumin) to an approximate concentration of 1 g/l.

The diagram in FIG. 1 discloses the glycation of the above-mentioned two solutions having a final glucose concentration of 1.5%. As can be seen from the diagram, there is substantially no difference in the glycation rates between the two solutions.

In FIG. 2, the same PD solutions as in FIG. 1 are shown relative to protein fluorescence generation, reflecting AGE formation according to the method described in the above-mentioned article "In vitro formation of advanced glycation end products in peritoneal dialysis fluid." As can clearly be seen, the standard PD fluid has a markedly higher generation of protein fluorescence, compared to the PD-BIO solution.

It is known that pyrraline is a marker for the presence of AGE products. As shown in table I below, the formation of pyrraline was measured for three different solutions, the PD-BIO solution, a conventional PD solution GAMBROSOL and a sterile filtered solution of the same composition as the GAMBROSOL solution, all having a glucose concentration of 4% and the same electrolyte composition as give above.

The samples were incubated for 16 hours or 7 days, at 37° C. under sterile conditions with human serum albumin (A) at a concentration of 40 g/l and without or with addition of 400 mmol/l glucose (G).

TABLE I

| | | pyrraline | |
|---|---|---|---|
| sample | incubation time | µg/g protein | pmol/mg protein |
| PD-BIO | | | |
| 16-A | 16 h | 17 | 67 |
| 7-A | 7 days | 22 | 88 |
| 16-GA | 16 h | 19 | 74 |
| 7-GA | 7 days | 23 | 89 |
| GAMBROSOL | | | |
| 16-A | 16 h | 25 | 97 |
| 7-A | 7 days | 75 | 294 |
| 16-GA | 16 h | 24 | 94 |
| 7-GA | 7 days | 65 | 257 |
| Sterile filtered | | | |
| 16-A | 16 h | 17 | 66 |
| 7-A | 7 days | 16 | 65 |
| 16-GA | 16 h | 16 | 63 |
| 7-GA | 7 days | 22 | 86 |

As can be seen from table I, the formation of pyrraline increased by a factor of 3 between the 16 hour incubation and the 7 day inhibition for the GAMBROSOL solution, but was substantially unchanged for the PD-BIO solution and the filtered GAMBROSOL solution.

Although not intended to be limited by any particular theory or hypothesis, it is believed that the above-mentioned data is indicative of the fact that conventional PD solutions sterilised in autoclaves in the final mixed composition, form degradation products of glucose acting as promoters for AGE formation. By the sterilisation method used in the PD-BIO solution, the concentration of such promoters is substantially reduced. This theory seems to be confirmed by the fact that sterile filtered PD solutions of the same composition as the GAMBROSOL solution and the PD-BIO solution do not substantially form pyrraline, as shown in table I.

In table II there is also shown the formation of fructose lysine and pentosidine after 7 days incubation. There seems to be no difference between the three solutions in this regard. Fructose lysine and pentosidine are also markers for AGE products. The conditions were the same as for table I.

TABLE II

| sample | fructose lysine | | pentosidine | |
|---|---|---|---|---|
| | nmol/mg HSA | mmol/mol HSA | pmol/mg HSA | mmol/mol HSA |
| PD-BIO | | | | |
| 7-GA | 79.0 | 5270 | 9.2 | 0.61 |
| 7-A | 35.9 | 2390 | 9.5 | 0.63 |
| GAMBROSOL | | | | |
| 7-GA | 77.6 | 5170 | 10.5 | 0.70 |
| 7-A | 31.2 | 2080 | 9.6 | 0.64 |
| sterile filtered | | | | |
| 7-GA | 73.6 | 4910 | 9.4 | 0.63 |
| 7-A | 36.5 | 2430 | 9.1 | 0.61 |

In order to find out which components in the peritoneal dialysis solution are responsible for the AGE formation, a series of experiments were carried out, in which a sterile filtered PD solution according to the above specification was used. To the samples of the solution were added human serum albumin at 40 mg/ml as the target protein for AGE formation. In the different samples were added glucose degradation products in different amounts typically found in heat sterilised conventional peritoneal dialysis fluids. The samples were incubated over 0, 1, 10 or 30 days and the AGE formation was measured by fluorescence measurements as in FIG. 2. The results appear from table III below.

TABLE III

| | t0 | t1 | t10 | t30 |
|---|---|---|---|---|
| Sterile filtered fluid | 150 | 154 | 169 | 196 |
| addition of acetaldehyde | | | | |
| 420 μmol | 160 | 169 | 177 | 198 |
| 1573 μmol | 166 | 173 | 188 | 218 |
| addition of formaldehyde | | | | |
| 15 μmol | 164 | 171 | 179 | 197 |
| 44 μmol | 165 | 171 | 181 | 201 |
| addition of methylglyoxal | | | | |
| 23 μmol | 162 | 165 | 162 | 194 |
| 164 μmol | 154 | 177 | 262 | 295 |

TABLE III-continued

| | t0 | t1 | t10 | t30 |
|---|---|---|---|---|
| addition of 5-HMF | | | | |
| 30 μmol | 157 | 156 | 164 | 193 |
| 1355 μmol | 157 | 156 | 176 | 219 |
| Autoclaved PD fluid | 160 | 217 | 318 | 371 |

As appears from table III, there seems to be a clear correlation between autoclaved PD fluids and AGE product formation as indicated by fluorescence. It appears that methylglyoxal also mediates AGE product formation, while the other substances do not seem to have much influence on such production in the used concentrations.

It is known that dicarbonyl compounds and specifically 3-deoxyglucosone, 3-DG, are formed during heat sterilisation of peritoneal dialysis solutions as a glucose degradation product. 3-DG is known to be a potent cross-linker. 3-DG is a highly reactive dicarbonyl intermediate of the Maillard reactions and a precursor of the advanced glycosylation end products, AGEs, such as pyrraline. The production of 3-DG normally starts from glucose which forms a Schiffs base after reaction with the amino group of a protein. The next step in the Maillard reactions is rearrangement to Amadori products which than in the late Maillard reactions split to form 3-DG. However, 3-DG has also been suggested as a possible intermediate in the degradation of carbohydrates by acids to 2-furaldehyde. If this is possible, 3-DG could appear in fresh fluid for peritoneal dialysis as a glucose degradation product. We have found that dicarbonyl compounds are suppressed at least tenfold in the PD-BIO solution compared to the GAMBROSOL solution.

The above-mentioned data is given for solutions intended to be used for peritoneal dialysis. When such solutions are installed into a patient undergoing peritoneal dialysis treatment, the solution comes into contact with a great number of different proteins prevailing in the peritoneal cavity. Moreover, the solution is diluted with solution already present in the abdominal cavity. Finally, an exchange of electrolytes and molecules take place inside the cavity and notably with the blood through the peritoneal membrane.

During the exposure of the peritoneal cavity to PD solutions having an unphysiologically high concentration of glucose, it is likely that proteins present in the cavity undergo similar reactions as seen in the above examples. Such altered proteins are transported from the abdominal cavity via the peritoneal membrane to the blood and to the rest of the body.

By using a PD solution having a low concentration of promoters of late stage advanced glycosylation end products, it is likely that adverse effects on the peritoneal membrane can be avoided as well as other complications associated with the generation of AGE products.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for the peritoneal dialysis of a patient susceptible to complications from advanced glycosylation end products comprising preparing a peritoneal dialysis solution by sterilizing a substantially pure glucose solution having a concentration of greater than about 20%, separately preparing a substantially glucose-free composition, and mixing said substantially pure sterilized glucose solution in said substantially glucose-free composition, to produce a solution having a reduced formation of said advanced glycosylation end products.

2. The method of claim 1, wherein said patient comprises a diabetic patient.

3. The method of claim 2, wherein said substantially pure sterilized glucose polymer solution has a concentration of greater than about 40%.

4. A method for the peritoneal dialysis of a patient susceptible to complications from advanced glycosylation end products comprising preparing a peritoneal dialysis solution by filter sterilizing a substantially pure glucose solution, separately preparing a substantially glucose-free composition, and mixing said substantially pure filter sterilized glucose solution in said substantially glucose-free composition to produce a solution having a reduced formation of said advanced glycosylation end products.

5. The method of claim 4, wherein said patient comprises a diabetic patient.

* * * * *